(12) United States Patent
Barve et al.

(10) Patent No.: US 12,329,468 B1
(45) Date of Patent: Jun. 17, 2025

(54) APPARATUS AND METHODS FOR IDENTIFICATION OF MEDICAL FEATURES

(71) Applicant: Anumana, Inc., Cambridge, MA (US)

(72) Inventors: Rakesh Barve, Bengaluru (IN); Suthirth Vaidya, Bengaluru (IN)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/787,453

(22) Filed: Jul. 29, 2024

(51) Int. Cl.
 *A61B 34/00* (2016.01)
 *A61B 34/10* (2016.01)
 (Continued)

(52) U.S. Cl.
 CPC ............ *A61B 34/25* (2016.02); *A61B 34/10* (2016.02); *G06T 7/0012* (2013.01); *G06T 7/70* (2017.01);
 (Continued)

(58) Field of Classification Search
 CPC ... A61B 34/30; A61B 34/20; A61B 2090/364; A61B 2090/365; A61B 1/000094; A61B 2034/105; A61B 1/018; A61B 2018/00577; A61B 34/10; A61B 34/25; A61B 2034/252; G16H 30/20; G16H 30/40; G16H 40/20; G16H 50/20; G06T 2207/30004; G06T 2207/10132; G06T 7/0012; G06T 7/00; G06T 7/0014; G06T 7/70; G06T 2207/20081; G06T 2207/30048; H04N 7/181; H04N 7/183; G06N 20/00; G06N 3/08; G06V 10/803; G06V 2201/034;
 (Continued)

(56) References Cited

U.S. PATENT DOCUMENTS

| 6,556,695 B1 | 4/2003 | Ben-Jaacov et al. |
| 9,931,790 B2 * | 4/2018 | Grbic ............... G06T 7/136 |

(Continued)

FOREIGN PATENT DOCUMENTS

| KR | 20220118685 A * | 8/2022 | |
| WO | WO-2015135056 A1 * | 9/2015 | ......... A61B 17/3421 |
| WO | 2024054935 A1 | 3/2024 | |

OTHER PUBLICATIONS

Machine translation obtained from google patents of KR20220118685A (Year: 2022).*

*Primary Examiner* — Aaron W Carter
*Assistant Examiner* — Courtney Joan Nelson
(74) *Attorney, Agent, or Firm* — Caldwell Intellectual Property Law

(57) ABSTRACT

Apparatus for identification of medical features and methods used therein include an ultrasonic imaging system configured to detect at least a query image containing ultrasound data pertaining to a subject, an intervention system configured to perform a concurrent medical procedure as a function of the detection of the at least a query image, a display device, a processor, and a memory communicatively connected to the processor, wherein the memory contains instructions configuring the processor to receive, from the ultrasonic imaging system, the at least a query image, identify the pose of an anatomical structure as a function of the at least a query image, determine at least a medical feature as a function of the pose of the anatomical structure, and suggest, using the display device, a modification to the concurrent medical procedure as a function of the at least a medical feature.

20 Claims, 9 Drawing Sheets

(51) Int. Cl.
  *G06T 7/00* (2017.01)
  *G06T 7/70* (2017.01)
  *G06V 10/40* (2022.01)
  *G06V 10/774* (2022.01)
(52) U.S. Cl.
  CPC ............ *G06V 10/40* (2022.01); *G06V 10/774* (2022.01); *A61B 2034/252* (2016.02); *G06T 2207/10132* (2013.01); *G06T 2207/20081* (2013.01); *G06T 2207/30048* (2013.01)
(58) Field of Classification Search
  CPC .. G06V 2201/03; G06V 10/40; G06V 10/774; G06F 30/27
  See application file for complete search history.

(56) References Cited

U.S. PATENT DOCUMENTS

| | | | | |
|---|---|---|---|---|
| 11,553,900 | B2* | 1/2023 | White | A61B 8/5284 |
| 11,589,928 | B2* | 2/2023 | Boddington | G16H 70/20 |
| 2005/0014995 | A1* | 1/2005 | Amundson | A61B 90/36 |
| | | | | 600/105 |
| 2005/0203502 | A1 | 9/2005 | Boveja et al. | |
| 2015/0374259 | A1* | 12/2015 | Garbey | G06Q 10/0639 |
| | | | | 600/424 |
| 2021/0065870 | A1* | 3/2021 | Spooner | G16H 50/70 |

* cited by examiner

APPARATUS AND METHODS FOR IDENTIFICATION OF MEDICAL FEATURES

FIELD OF THE INVENTION

The present invention generally relates to the field of clinical decision support. In particular, the present invention is directed to apparatus and methods for identification of medical features.

BACKGROUND

Many medical procedures involve invasive and potentially harmful techniques such as fluoroscopy. As a result, patients undergoing such procedures often need to endure significant risk and discomfort. In addition, these medical procedures typically require separate diagnostic and treatment steps that are incapable of capturing emergent findings during the procedure, which potentially increases the likelihood of accidents and limits the success rate.

SUMMARY OF THE DISCLOSURE

In an aspect, an apparatus for identification of medical features is described. Apparatus includes an ultrasonic imaging system configured to detect at least a query image containing ultrasound data pertaining to a subject, an intervention system configured to perform a concurrent medical procedure as a function of the detection of the at least a query image, and a display device. In addition, apparatus includes a processor and a memory communicatively connected to the processor, wherein the memory contains instructions configuring the processor to receive, from ultrasonic imaging system, at least a query image, identify a pose of an anatomical structure as a function of the at least a query image, determine at least a medical feature as a function of the pose of the anatomical structure, wherein determining the at least a medical feature includes receiving feature training data including a plurality of training images as input and a plurality of labelled features as output, training an image processing machine learning model including a plurality of image processing algorithms using the feature training data, and determining the at least a medical feature as a function of the at least a query image using the trained image processing machine learning model, and suggest, using display device, a modification to concurrent medical procedure as a function of the at least a medical feature.

In another aspect, a method for identification of medical features is described. Method includes detecting, using ultrasonic imaging system, at least a query image containing ultrasound data pertaining to subject, performing, using intervention system, concurrent medical procedure as a function of the detection of the at least a query image, receiving, by processor from the ultrasonic imaging system, the at least a query image, identifying, by the processor, pose of the anatomical structure as a function of the at least a query image, determining, by the processor, at least a medical feature as a function of the pose of the anatomical structure, wherein determining the at least a medical feature includes receiving feature training data including plurality of training images as input and plurality of labelled features as output, training image processing machine learning model including plurality of image processing algorithms using the feature training data, and determining the at least a medical feature as a function of the at least a query image using the trained image processing machine learning model, and suggesting, by the processor using display device, modification to the concurrent medical procedure as a function of the at least a medical feature.

These and other aspects and features of nonlimiting embodiments of the present invention will become apparent to those skilled in the art upon review of the following description of specific nonlimiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatus and methods for identification of medical features using ultrasound images. In one or more embodiments, apparatus may include an ultrasonic imaging system, such as one or more ultrasound transducers, configured to detect at least a query image containing ultrasound data pertaining to a subject, an intervention system, such as an ablation catheter, configured to perform a medical procedure, such as cardiac ablation, concurrent with the detection of the at least a query image, and a display device. In addition, apparatus may include a processor and a memory communicatively connected to the processor, wherein the memory contains instructions configuring the processor to receive, from ultrasonic imaging system, at least a query image, identify a pose of an anatomical structure as a function of the at least a query image, determine at least a medical feature, such as a case of calcification at a heart valve, a thrombus in the left atrial appendage, one or more abnormal heart valve movements or functions, and a thickness such as a heart wall thickness, among others, as a function of the pose of the anatomical structure, using an image processing machine learning model, and suggest, using display device, a modification to concurrent medical procedure as a function of the at least a medical feature.

Aspects of the present disclosure may be used to provide real-time, adaptive clinical decision support during a medical procedure, such as cardiac ablation, without exposing patients to repeated discomfort. Aspects of the present disclosure may be used to promote a use of noninvasive or minimally invasive clinical tools for such medical procedure. Aspects of the present disclosure may be used to support image-guided surgery and therapy. Exemplary embodiments illustrating aspects of the present disclosure are described below in the context of several specific examples.

Figure 1:
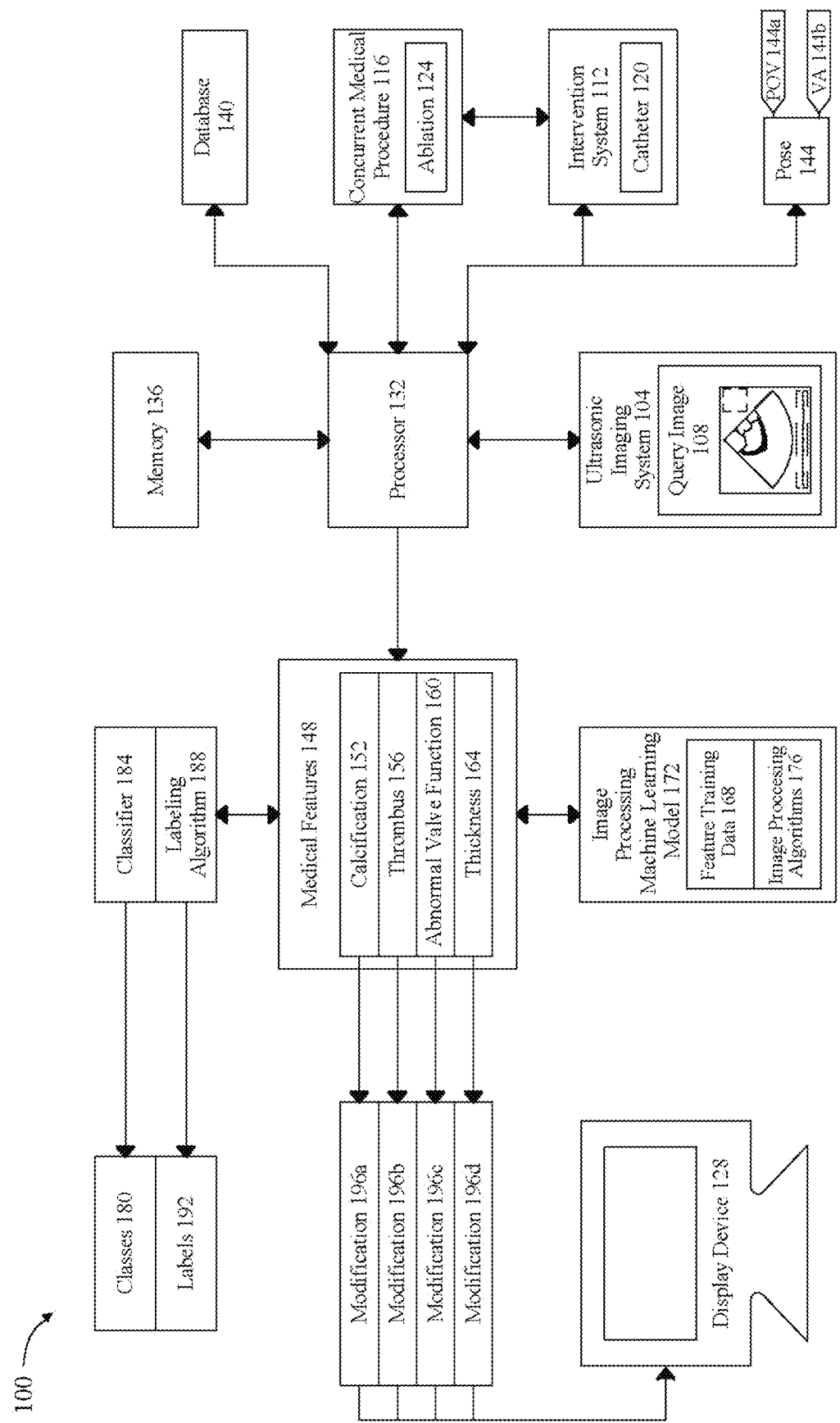
FIG. 1 is an exemplary embodiment of an apparatus for identifying medical features.

Referring now to FIG. 1, an apparatus 100 for identifying medical features is illustrated. Apparatus 100 includes an ultrasonic imaging system 104 configured to detect at least a query image 108 comprising ultrasound data pertaining to a subject. For the purposes of this disclosure, an "ultrasonic imaging system" is an image capture device capable of capturing at least an ultrasound image. In some cases, ultrasonic imaging system 104 may render a graphic representation of a three-dimensional (3D) object by sending ultrasound waves and detecting their reflections as they interact with a plurality of features or structures with various values of density and/or reflectivity within the 3D object. In some cases, 3D object may include an organ such as a heart with complex internal structures including walls, chambers, blood vessels, among others. In some cases, 3D object may include a tissue. For the purposes of this disclosure, an "image capture device" is a device capable of recording a digital representation of an object. Image capture device may include any type of image capture device accessible to a person of ordinary skill in the art, and/or deemed suitable by a person of ordinary skill in the art upon reviewing the entirety of this disclosure. In one or more embodiments, image capture device may include a camera. For the purposes of this disclosure, a "camera" is a single device or an assembly of multiple devices configured to detect at least one type of electromagnetic radiation and generate a graphical representation therefrom. As nonlimiting examples, camera may detect visible light, infrared light, ultraviolet light, or X-ray. In one or more embodiments, camera may include one or more optics; nonlimiting examples of optics include spherical lenses, aspherical lenses, reflectors, polarizers, filters, windows, aperture stops, and the like. In one or more embodiments, camera may include an image sensor. Exemplary image sensors include digital image sensors, such as without limitation charge-coupled device (CCD) sensors and complimentary metal-oxide-semiconductor (CMOS) sensors. As a nonlimiting example, camera may include a remote camera device communicatively connected to a computing device, such as a portable camera connected to a desktop or laptop computer through either a cord or wireless connection. As a nonlimiting example, camera may include a camera integrated within a computing device, such as a built-in camera of a laptop computer. As another nonlimiting example, camera may include a camera integrated within a remote and/or portable device, such as a built-in camera of a smartphone or a tablet.

With continued reference to FIG. 1, ultrasonic imaging system 104 may include at least an ultrasound transducer. For the purposes of this disclosure, an "ultrasound transducer" is a device capable of generating and/or receiving ultrasound waves or ultrasound signals. In some cases, ultrasound transducer may include one or more transmitters capable of converting electric signals into ultrasound waves. In some cases, ultrasound transducer may include one or more receivers capable of converting ultrasound waves into electrical signals. Additionally and/or alternatively, ultrasound transducer may include one or more transceivers capable of both transmitting and receiving ultrasound waves. "Ultrasound transducer" and "ultrasound probe" may be used interchangeably throughout this disclosure. For the purposes of this disclosure, a "signal" is an intelligible representation of data, for example from one device to another. A signal may include an optical signal, a hydraulic signal, a pneumatic signal, a mechanical signal, an electric signal, a digital signal, an analog signal, and the like. In some cases, a signal may be used to communicate with a computing device, for example by way of one or more ports. In some cases, a signal may be transmitted and/or received by a computing device for example by way of an input/output port. An analog signal may be digitized, for example by way of an analog to digital converter. In some cases, an analog signal may be processed, for example by way of any analog signal processing steps described in this disclosure, prior to digitization. In some cases, a digital signal may be used to communicate between two or more devices, including without limitation computing devices. In some cases, a digital signal may be communicated by way of one or more communication protocols, including without limitation internet protocol (IP), controller area network (CAN) protocols, serial communication protocols (e.g., universal asynchronous receiver-transmitter [UART]), parallel communication protocols (e.g., IEEE 128 [printer port]), and the like.

With continued reference to FIG. 1, for the purposes of this disclosure, an "image" is a visual representation of data. In one or more embodiments, image may be a product of image capture device described above. In one or more embodiments, image may contain digital information representing at least a physical scene, space, and/or object. In one or more embodiments, image may be an optical image, such as without limitation an image of an object generated by at least an optic. In some cases, image may be a digital representation of another image, such as a digital image of a printed photograph or the like captured using a built-in camera of a smartphone. Alternatively, image may comprise a plurality of images arranged in sequence as a function of time, such as one or more videos. In some embodiments, image may include a digital image. Digital image may be in a format such as jpeg, png, pdf, btmp, and the like. For the purposes of this disclosure, a "query image" is an image containing data or information that may be used as a query to match other data or information and/or to selectively retrieve data or information for use in further method steps as disclosed below.

With continued reference to FIG. 1, for the purposes of this disclosure, ultrasound data are data collected using ultrasound imaging system 104 that contain medically relevant information. In some cases, ultrasound data may include an electrocardiogram. For the purposes of this disclosure, an "echocardiogram" is an ultrasound image specifically pertaining to the heart of a subject and generated using ultrasonic imaging system 104, as described above. Accordingly, the imaging technique used to collect echocardiograms may be called "echocardiography". Exemplary types of echocardiography include intracardiac echocardiography, point-of-care ultrasound, transthoracic echocardiography, transesophageal echocardiography, stress echocardiography, and intravascular ultrasound, among others. In one or more embodiments, echocardiogram may include an intracardiac echocardiogram (ICE). For the purposes of this disclosure, an "intracardiac echocardiogram (ICE)" is a two-dimensional (2D) ultrasound image collected by inserting, using a catheter, an ultrasound transducer inside a heart. It represents the anatomy (i.e., walls, chambers, blood vessels, etc.) of at least part of a heart. In some cases, ICE may be collected by crossing the interatrial septum with a transseptal puncture to permit catheter access from the right atrium to the left atrium; alternatively, catheter may access the left heart by retrograding through the aorta and passing the aortic valve to enter the left ventricle. For the purposes of this disclosure, a "catheter" is a medical device comprising a thin, flexible tube made from medical-grade materials that may be inserted into part of a patient's body. Given its reduced size and flexible, noninvasive nature, a catheter may be configured to perform various functions such as collecting or transferring a clinical sample, administering a medicine or nutrient, providing a treatment for a disease, or performing a surgical procedure. Catheters are often manufactured for specific applications, such as cardiovascular, urological, gastrointestinal, neurovascular, and ophthalmic procedures.

With continued reference to FIG. 1, ultrasound data may include a point-of-care ultrasound (POCUS). For the purposes of this disclosure, a "point-of-care ultrasound (POCUS)" is an ultrasound image collected using a medical technique that involves a portable, user-operated diagnostic imaging device and enables healthcare providers to perform real-time ultrasound examinations at the patient's bedside or in remote settings, without the need for specialized radiology departments. POCUS allows for immediate visualization of internal structures and organs, facilitating rapid diagnosis, treatment decisions, and monitoring of various medical conditions. POCUS devices typically feature compact designs, integrated transducers, and user-friendly interfaces, enabling non-radiologist clinicians to obtain high-quality images. Applications of POCUS may include, but are not limited to, assessing cardiac function, detecting fluid collections, guiding needle placements, and evaluating trauma patients. The portability and ease of use of POCUS devices may significantly enhance clinical workflow, improve patient outcomes, and expand access to diagnostic imaging in diverse healthcare environments.

With continued reference to FIG. 1, in one or more embodiments, echocardiogram may include a transthoracic echocardiogram (TTE). For the purposes of this disclosure, a "transthoracic echocardiogram (TTE)" is a 2D ultrasound image of a heart collected by placing an ultrasound probe or ultrasound transducer on a patient's chest or abdomen to collect various views of a heart. In one or more embodiments, echocardiogram may include a transesophageal echocardiogram (TEE). For the purposes of this disclosure, a "transesophageal echocardiogram (TEE)" is a 2D ultrasound image of a heart collected by passing a specialized probe or catheter containing an ultrasound transducer at its tip into a patient's esophagus.

With continued reference to FIG. 1, for the purposes of this disclosure, a "subject" or "patient" is a human or any individual organism, on whom or on which a procedure, study, or otherwise experiment, may be conducted. As nonlimiting examples, patient may include human patient with symptoms of atrial or ventricular fibrillation and/or undergoing cardiac ablation, an individual undergoing cardiac screening, a participant in a clinical trial, an individual with congenital heart disease, a heart transplant candidate, an individual receiving follow-up care after cardiac surgery, a healthy volunteer, an individual with heart failure, or the like. Additionally and/or alternatively, patient may include a pet or an animal model (i.e., an animal used to model certain medical conditions such as a laboratory rat).

With continued reference to FIG. 1, apparatus 100 includes an intervention system 112 configured to perform a concurrent medical procedure 116 as a function of the detection of at least a query image 108. For the purposes of this disclosure, an "intervention system" is a system equipped with one or more medical tools that may be used to perform one or more acts of correction or treatment. For the purposes of this disclosure, a "concurrent medical procedure" is a medical procedure performed with a time span that is either synchronized or overlapping with the detection of at least a query image 108. In one or more embodiments, accordingly, apparatus 100 may be configured to be capable of providing clinical decision support or guidance in a real-time or nearly real-time manner. In one or more embodiments, intervention system 112 may include a catheter 120, as described above, configured to perform an ablation procedure 124. For the purposes of this disclosure, an "ablation procedure" is a medical procedure that involves the removal or destruction of tissue. Ablation may be used for organs such as liver, lung, kidney, thyroid, prostate, uterus, or the like. As nonlimiting examples, ablation procedure may be utilized for treating irregular heartbeats, liver tumors, lung tumors, kidney tumors, thyroid nodules, prostate cancer, and for endometrial ablation in the uterus to address heavy menstrual bleeding. Different ablation methods include radiofrequency, microwave, laser, and cryoablation, each suited to specific medical conditions and types of tissue. For the purposes of this disclosure, a "cardiac ablation procedure" is a type of ablation procedure used for treatment of irregular heartbeats (i.e., arrhythmias). A cardiac ablation procedure often uses heat or cold to create tiny scars in a heart that block faulty heart signals and help restore a healthy heartbeat. Ablation procedures that use heat are termed radiofrequency (RF) ablations or rhizotomies, whereas ablation procedures that use cold are termed cryoablations instead. In some cases, ablation procedure may include a pulse field ablation procedure, which is a relatively new ablation procedure that induces programed cell death (i.e., apoptosis). In some cases, ablation procedure may include a plurality of dosage parameters. Ablation procedure is most often done using catheters that are inserted through a blood vessel. Typical cases of arrhythmias that may potentially be treated using ablation procedures include atrial fibrillation, ventricular fibrillation, atrial flutter, and Wolff-Parkinson-White syndrome, among others. For the purposes of this disclosure, "atrial fibrillation" is a medical condition of an irregular (and often very rapid) heart rhythm in the upper chambers of a heart (i.e., the two atria); as a result, blood doesn't flow as well as it should from the atria to the lower chambers of the heart (i.e., the two ventricles). Atrial fibrillation may lead to blood clots in the heart and may increase the risk of stroke, heart failure, and other heart-related complications. Atrial fibrillation may be contrasted to ventricular fibrillation, wherein it is the lower heart chambers (i.e., the two ventricles) of a heart that contract in a very rapid and uncoordinated manner instead; as a result, the heart doesn't pump blood efficiently to the rest of the body.

With continued reference to FIG. 1, apparatus 100 includes a display device 128. For the purposes of this disclosure, a "display device" is a device configured to show visual information. In some cases, display device 128 may include a liquid crystal display (LCD), a cathode ray tube (CRT), a plasma display, a light emitting diode (LED) display, and/or any combinations thereof. Display device 128 may include, but is not limited to, a smartphone, tablet, laptop, monitor, tablet, and the like. Display device 128 may include a separate device that includes a transparent screen configured to display computer-generated images and/or information. In one or more embodiments, display device 128 may be configured to visually present data through a user interface or a graphical user interface (GUI) to at least a user, wherein the user may interact with the data through the user interface or GUI, as described below. In one or more embodiments, a user may view GUI through display device 128. In one or more embodiments, display device 128 may be located on or combined with a remote device, as described below. Additional details will be provided below in this disclosure through nonlimiting examples.

With continued reference to FIG. 1, display device 128 may include a remote device. For the purposes of this disclosure, a "remote device" is a computer device separate and distinct from apparatus 100. For example, and without limitation, remote device may include a smartphone, a tablet, a laptop, a desktop computer, or the like. In one or more embodiments, remote device may be communicatively connected to apparatus 100 such as, for example, through network communication, through Bluetooth communication, and/or the like. In one or more embodiments, a processor may receive query image 108 and/or initiate one or more of subsequent steps through remote device. In one or more embodiments, one or more inputs from one or more entities may be submitted through a user interface, such as a GUI, displayed using remote device, as described below.

With continued reference to FIG. 1, apparatus 100 includes a processor 132. In one or more embodiments, processor 132 may include a computing device. Computing device could include any analog or digital control circuit, including an operational amplifier circuit, a combinational logic circuit, a sequential logic circuit, an application-specific integrated circuit (ASIC), a field programmable gate arrays (FPGA), or the like. Computing device may include a processor communicatively connected to a memory, as described above. Computing device may include any computing device as described in this disclosure, including without limitation a microcontroller, microprocessor, digital signal processor, and/or system on a chip as described in this disclosure. Computing device may include, be included in, and/or communicate with a mobile device such as a mobile telephone, smartphone, or tablet. Computing device may include a single computing device operating independently, or may include two or more computing device operating in concert, in parallel, sequentially, or the like; two or more computing devices may be included together in a single computing device or in two or more computing devices. Computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device may include but is not limited to, for example, a first computing device or cluster of computing devices in a first location and a second computing device or cluster of computing devices in a second location. Computing device may include one or more computing devices dedicated to data storage, security, distribution of traffic for load balancing, and the like. Computing device may distribute one or more computing tasks as described below across a plurality of computing devices of computing device, which may operate in parallel, in series, redundantly, or in any other manner used for distribution of tasks or memory between computing devices. Computing device may be implemented, as a non-limiting example, using a "shared nothing" architecture.

With continued reference to FIG. 1, computing device may be designed and/or configured to perform any method, method step, or sequence of method steps in any embodiment described in this disclosure, in any order and with any degree of repetition. For instance, computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. A person of ordinary skill in the art, upon reviewing the entirety of this disclosure, will be aware of various ways in which steps, sequences of steps, processing tasks, and/or data may be subdivided, shared, or otherwise dealt with using iteration, recursion, and/or parallel processing. More details regarding computing devices will be described below.

With continued reference to FIG. 1, apparatus 100 includes a memory 136 communicatively connected to processor 132, wherein the memory 136 contains instructions configuring the processor 132 to perform any processing steps described herein. For the purposes of this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, using a bus or other facility for intercommunication between elements of a computing device. Communicative connecting may also include indirect connections via, for example and without limitation, wireless connection, radio communication, low-power wide-area network, optical communication, magnetic, capacitive, or optical coupling, and the like. In some instances, the terminology "communicatively coupled" may be used in place of communicatively connected in this disclosure.

With continued reference to FIG. 1, computing device may perform determinations, classification, and/or analysis steps, methods, processes, or the like as described in this disclosure using machine learning processes. For the purposes of this disclosure, a "machine learning process" is a process that automatedly uses a body of data known as "training data" and/or a "training set" to generate an algorithm that will be performed by a processor module to produce outputs given data provided as inputs; this is in contrast to a nonmachine learning software program where the commands to be executed are determined in advance by a user and written in a programming language. A machine learning process may utilize supervised, unsupervised, lazy-learning processes and/or neural networks. More details regarding computing devices and machine learning processes will be provided below.

With continued reference to FIG. 1, in one or more embodiments, one or more machine learning models may be used to perform certain function or functions of apparatus 100, such as determination of at least a medical feature, as described below. For the purposes of this disclosure, a "medical feature" is a structural or functional characteristic that describes one or more aspects regarding a patient's health. Exemplary medical features related to apparatus 100 will be described in detail below in this disclosure. Processor 132 may use a machine learning module to implement one or more algorithms as described herein or generate one or more machine learning models, such as image processing model, as described below. However, machine learning module is exemplary and may not be necessary to generate one or more machine learning models and perform any machine learning described herein. In one or more embodiments, one or more machine learning models may be generated using training data. Training data may include inputs and corresponding predetermined outputs so that machine learning model may use correlations between the provided exemplary inputs and outputs to develop an algorithm and/or relationship that then allows the machine learning model to determine its own outputs for inputs. Training data may contain correlations that a machine learning process may use to model relationships between two or more categories of data elements. Exemplary inputs and outputs may be retrieved from a database, extracted from medical literature, selected from one or more electronic health records (EHRs), be provided by a user such as a medical professional, or synthesized using a generative machine learning model, as described below. In one or more embodiments, machine learning module may obtain training data by querying a communicatively connected database that includes past inputs and outputs. Training data may include inputs from various types of databases, resources, and/or user inputs and outputs correlated to each of those inputs, so that machine learning model may determine an output. Correlations may indicate causative and/or predictive links between data, which may be modeled as relationships, such as mathematical relationships, by machine learning models, as described in further detail below. In one or more embodiments, training data may be formatted and/or organized by categories of data elements by, for example, associating data elements with one or more descriptors corresponding to categories of data elements. As a nonlimiting example, training data may include data entered in standardized forms by persons or processes, such that entry of a given data element in a given field in a form may be mapped to one or more descriptors of categories. Elements in training data may be linked to descriptors of categories by tags, tokens, or other data elements. In one or more embodiments, training data may include previous outputs such that one or more machine learning models may iteratively produce outputs.

With continued reference to FIG. 1, apparatus 100 may include or be communicatively connected to a database 140. For the purposes of this disclosure, a "database" is an organized collection of data or a type of data store based on the use of a database management system (DBMS), the software that interacts with end users, applications, and the database itself to capture and analyze the data. Database may be implemented, without limitation, as a relational database, a key-value retrieval database such as a NoSQL database, or any other format or structure for use as database that a person of ordinary skill in the art would recognize as suitable upon review of the entirety of this disclosure. Database may Alternatively and/or additionally be implemented using a distributed data storage protocol and/or data structure, such as a distributed hash table or the like. Database 140 may include a plurality of data entries and/or records as described in this disclosure. Data entries in database may be flagged with or linked to one or more additional elements of information, which may be reflected in data entry cells and/or in linked tables such as tables related by one or more indices in database or another relational database. A person of ordinary skill in the art, upon reviewing the entirety of this disclosure, will be aware of various ways in which data entries in database may store, retrieve, organize, and/or reflect data and/or records as used herein, as well as categories and/or populations of data consistently with this disclosure.

With continued reference to FIG. 1, apparatus 100 may include or be communicatively connected to one or more electronic health records (EHRs). For the purposes of this disclosure, an electronic health record (EHR) is a comprehensive collection of records relating to the health history, diagnosis, or condition of a patient, relating to treatment provided or proposed to be provided to the patient, or relating to additional factors that may impact the health of the patient; elements within an EHR, once combined, may provide a detailed picture of patient's overall health. In one or more embodiments, one or more query images 108 and/or one or more medical features determined therefrom may be deposited to and retrieved from one or more EHRs. In one or more embodiments, EHR may include demographic data of patient; for example, and without limitation, EHR may include basic information about patient such as name, age, gender, ethnicity, socioeconomic status, and/or the like. In one or more embodiments, each EHR may also include patient's medical history; for example, and without limitation, EHR may include a detailed record of patient's past health conditions, medical procedures, hospitalizations, and illnesses such as surgeries, treatments, medications, allergies, and/or the like. In one or more embodiments, each EHR may include lifestyle information of patient; for example, and without limitation, EHR may include details about the patient's diet, exercise habits, smoking and alcohol consumption, and other behaviors that could impact patient's health. In one or more embodiments, EHR may include patient's family history; for example, and without limitation, EHR may include a record of hereditary diseases. In one or more embodiments, database 140 may comprise a plurality of EHRs. In one or more embodiments, EHRs may be retrieved from a repository of similar nature as database 140.

With continued reference to FIG. 1, in one or more embodiments, machine learning module may be further configured to generate a multimodal neural network that combines various neural network architectures described herein. In a nonlimiting example, multimodal neural network may combine LSTM for time-series analysis with GPT models for natural language processing. Such fusion may be applied by processor 132 and/or computing device to generate synthetic images, medical features, or the like. In one or more embodiments, multimodal neural network may also include a hierarchical multimodal neural network, wherein the hierarchical multimodal neural network may involve a plurality of layers of integration. For instance, and without limitation, different models may be combined at various stages of the network. Convolutional neural network (CNN) may be used for image feature extraction, followed by LSTMs for sequential pattern recognition, and a MDN at the end for probabilistic modeling. Other exemplary embodiments of multimodal neural network may include, without limitation, ensemble-based multimodal neural network, cross-modal fusion, adaptive multimodal network, among others. A person of ordinary skill in the art, upon reviewing the entirety of this disclosure, will be aware of various multimodal neural networks and combination thereof that may be implemented by apparatus 100 in accordance with this disclosure.

With continued reference to FIG. 1, in one or more embodiments, processor 132 may perform one or more functions of apparatus 100, such as training an image processing machine learning model, as described below, by using optical character recognition (OCR) to read digital files and extract information therein. In one or more embodiments, OCR may include automatic conversion of images (e.g., typed, handwritten, or printed text) into machine-encoded text. In one or more embodiments, recognition of at least a keyword from an image component may include one or more processes, including without limitation OCR, optical word recognition, intelligent character recognition, intelligent word recognition, and the like. In one or more embodiments, OCR may recognize written text one glyph or character at a time, for example, for languages that use a space as a word divider. In one or more embodiments, intelligent character recognition (ICR) may recognize written text one glyph or character at a time, for instance by employing machine learning processes. In one or more embodiments, intelligent word recognition (IWR) may recognize written text, one word at a time, for instance by employing machine learning processes.

With continued reference to FIG. 1, in one or more embodiments, OCR may employ preprocessing of image components. Preprocessing process may include without limitation de-skew, de-speckle, binarization, line removal, layout analysis or "zoning", line and word detection, script recognition, character isolation or "segmentation", and normalization. In one or more embodiments, a de-skew process may include applying a transform (e.g., homography or affine transform) to an image component to align text. In one or more embodiments, a de-speckle process may include removing positive and negative spots and/or smoothing edges. In one or more embodiments, a binarization process may include converting an image from color or greyscale to black-and-white (i.e., a binary image). Binarization may be performed as a simple way of separating text (or any other desired image component) from the background of image component. In one or more embodiments, binarization may be required for example if an employed OCR algorithm only works on binary images. In one or more embodiments, line removal process may include removal of non-glyph or non-character imagery (e.g., boxes and lines). In one or more embodiments, a layout analysis or "zoning" process may identify columns, paragraphs, captions, and the like as distinct blocks. In one or more embodiments, a line and word detection process may establish a baseline for word and character shapes and separate words, if necessary. In one or more embodiments, a script recognition process may, for example in multilingual documents, identify a script, allowing an appropriate OCR algorithm to be selected. In one or more embodiments, a character isolation or "segmentation" process may separate signal characters, for example, character-based OCR algorithms. In one or more embodiments, a normalization process may normalize the aspect ratio and/or scale of image component.

With continued reference to FIG. 1, in one or more embodiments, an OCR process may include an OCR algorithm. Exemplary OCR algorithms include matrix-matching processes and/or feature extraction processes. Matrix matching may involve comparing an image to a stored glyph on a pixel-by-pixel basis. In one or more embodiments, matrix matching may also be known as "pattern matching", "pattern recognition", and/or "image correlation". Matrix matching may rely on an input glyph being correctly isolated from the rest of image component. Matrix matching may also rely on a stored glyph being in a similar font and at the same scale as input glyph.

With continued reference to FIG. 1, in one or more embodiments, an OCR process may include a feature extraction process. In one or more embodiments, feature extraction may decompose a glyph into features. Exemplary nonlimiting features may include corners, edges, lines, closed loops, line direction, line intersections, and the like. In one or more embodiments, feature extraction may reduce the dimensionality of representation and may make the recognition process computationally more efficient. In one or more embodiments, extracted features can be compared with an abstract vector-like representation of a character, which might be reduced to one or more glyph prototypes. General techniques of feature detection in computer vision are applicable to this type of OCR. In one or more embodiments, machine learning process like nearest neighbor classifiers (e.g., k-nearest neighbors algorithm) can be used to compare image features with stored glyph features and choose a nearest match. OCR may employ any machine learning process described in this disclosure. Exemplary nonlimiting OCR software includes Cuneiform and Tesseract. Cuneiform is a multi-language, open-source OCR system originally developed by Cognitive Technologies of Moscow, Russia. Tesseract is a free OCR software originally developed by Hewlett-Packard of Palo Alto, California, United States.

With continued reference to FIG. 1, in one or more embodiments, OCR may employ a two-pass approach to character recognition. Second pass may include adaptive recognition and use letter shapes recognized with high confidence on a first pass to better recognize remaining letters on a second pass. In one or more embodiments, two-pass approach may be advantageous for unusual fonts or low-quality image components where visual verbal content may be distorted. Another exemplary OCR software tool includes OCRopus. The development of OCRopus is led by the German Research Center for Artificial Intelligence in Kaiserslautern, Germany. In one or more embodiments, OCR software may employ neural networks, for example, deep neural networks, as described in this disclosure below.

With continued reference to FIG. 1, in one or more embodiments, OCR may include post-processing. For example, OCR accuracy can be increased, in some cases, if output is constrained by a lexicon. A lexicon may include a list or set of words that are allowed to occur in a document. In one or more embodiments, a lexicon may include, for instance, all the words in the English language, or a more technical lexicon for a specific field. In some cases, an output stream may be a plain text stream or file of characters. In one or more embodiments, an OCR may preserve an original layout of visual verbal content. In one or more embodiments, near-neighbor analysis can make use of co-occurrence frequencies to correct errors by noting that certain words are often seen together. For example, "Washington, D.C." is generally far more common in English than "Washington DOC". In one or more embodiments, an OCR process may make use of a priori knowledge of grammar for a language being recognized. For example, OCR process may apply grammatical rules to help determine if a word is likely to be a verb or a noun. Distance conceptualization may be employed for recognition and classification. For example, a Levenshtein distance algorithm may be used in OCR post-processing to further optimize results. A person of ordinary skill in the art will recognize how to apply the aforementioned technologies to extract information from a digital file upon reviewing the entirety of this disclosure.

With continued reference to FIG. 1, in one or more embodiments, a computer vision module configured to perform one or more computer vision tasks such as, without limitation, object recognition, feature detection, edge/corner detection thresholding, or machine learning process may be used to recognize specific features or attributes. For the purposes of this disclosure, a "computer vision module" is a computational component designed to perform one or more computer vision, image processing, and/or modeling tasks. In one or more embodiments, computer vision module may receive one or more digital files containing one or more reference attributes from a data repository and generate one or more labels as a function of the received one or more reference attributes. In one or more embodiments, to generate a plurality of labels, computer vision module may be configured to compare one or more reference attributes against the statistical data of the one or more reference attributes and attach one or more labels as a function of the comparison, as described below.

With continued reference to FIG. 1, in one or more embodiments, computer vision module may include an image processing module, wherein images may be pre-processed using the image processing module. For the purposes of this disclosure, an "image processing module" is a component designed to process digital images such as images described herein. For example, and without limitation, image processing module may be configured to compile a plurality of images of a multi-layer scan to create an integrated image. In one or more embodiments, image processing module may include a plurality of software algorithms that can analyze, manipulate, or otherwise enhance an image, such as, without limitation, a plurality of image processing techniques as described below. In one or more embodiments, computer vision module may also include hardware components such as, without limitation, one or more graphics processing units (GPUs) that can accelerate the processing of a large number of images. In one or more embodiments, computer vision module may be implemented with one or more image processing libraries such as, without limitation, OpenCV, PIL/Pillow, ImageMagick, and the like. In a nonlimiting example, in order to generate one or more labels and/or recognize one or more reference attributes, one or more image processing tasks, such as noise reduction, contrast enhancement, intensity normalization, image segmentation, and/or the like, may be performed by computer vision module on a plurality of images to isolate certain features or components from the rest. In one or more embodiments, one or more machine learning models may be used to perform segmentations, for example, and without limitation, a U-net (i.e., a convolution neural network containing a contracting path as an encoder and an expansive path as a decoder, wherein the encoder and the decoder forms a U-shaped structure). A person of ordinary skill in the art, upon reviewing the entirety of this disclosure, will be aware of various image processing, computer vision, and modeling tasks that may be performed by processor 132.

With continued reference to FIG. 1, in one or more embodiments, one or more functions of apparatus 100 may involve a use of image classifiers to classify images within any data described in this disclosure. For the purposes of this disclosure, an "image classifier" is a machine learning model, such as a mathematical model, neural net, or program generated by a machine learning algorithm known as a "classification algorithm", as described in further detail below, that sort inputs of image information into categories or bins of data, outputting the categories or bins of data and/or labels associated therewith. Image classifier may be configured to output at least a datum that labels or otherwise identifies a set of images that are clustered together, found to be close under a distance metric as described below, or the like. Computing device and/or another device may generate image classifier using a classification algorithm. For the purposes of this disclosure, a classification algorithm is a process whereby computing device derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, Fisher's linear discriminant, quadratic classifiers, decision trees, boosted trees, random forest classifiers, learning vector quantization, and/or neural network-based classifiers. In one or more embodiments, processor 132 may use image classifier to identify a key image in any data described in this disclosure. For the purposes of this disclosure, a "key image" is an element of visual data used to identify and/or match elements to each other. In one or more embodiments, key image may include part of an ultrasound image such as an ICE with features that unambiguously identify the type of the ultrasound image. Image classifier may be trained with binarized visual data that have already been classified to determine key images in any other data described in this disclosure. For the purposes of this disclosure, "binarized visual data" are visual data that are described in a binary format. For example, binarized visual data of a photo may comprise ones and zeroes, wherein the specific sequence of ones and zeros may be used to represent the photo. Binarized visual data may be used for image recognition wherein a specific sequence of ones and zeroes may indicate a product present in the image. An image classifier may be consistent with any classifier as discussed herein. An image classifier may receive input data (e.g., training images) described in this disclosure and output a key image with the data. In one or more embodiments, image classifier may be used to compare visual data in one data set, such as query image 108, with visual data in another data set, such as one or more training images, as described below.

With continued reference to FIG. 1, processor 132 may be configured to perform feature extraction on query images 108 and/or one or more training images, as described below. For the purposes of this disclosure, "feature extraction" is a process of transforming an initial data set into informative measures and values. For example, feature extraction may include a process of determining one or more geometric features of an anatomic structure. In one or more embodiments, feature extraction may be used to determine one or more spatial relationships within a drawing that may be used to uniquely identify one or more features. In one or more embodiments, processor 132 may be configured to extract one or more regions of interest, wherein the regions of interest may be used to extract one or more features using one or more feature extraction techniques.

With continued reference to FIG. 1, processor 132 may be configured to perform one or more of its functions, such as determining at least a medical feature, as described below, using a feature learning algorithm. For the purposes of this disclosure, a "feature learning algorithm" is a machine learning algorithm that identifies associations between elements of data in a data set, which may include without limitation a training data set, where particular outputs and/or inputs are not specified. For instance, and without limitation, a feature learning algorithm may detect co-occurrences of elements of data, as defined above, with each other. Computing device may perform feature learning algorithm by dividing elements or sets of data into various sub-combinations of such data to create new elements of data and evaluate which elements of data tend to co-occur with which other elements. In one or more embodiments, feature learning algorithm may perform clustering of data.

With continued reference to FIG. 1, feature learning and/or clustering algorithm may be implemented, as a non-limiting example, using a k-means clustering algorithm. For the purposes of this disclosure, a "k-means clustering algorithm" is a type of cluster analysis that partitions n observations or unclassified cluster data entries into k clusters in which each observation or unclassified cluster data entry belongs to the cluster with the nearest mean. For the purposes of this disclosure, "cluster analysis" is a process that includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering, whereby each observation or unclassified cluster data entry belongs to a cluster or not. Cluster analysis may include soft clustering or fuzzy clustering, whereby each observation or unclassified cluster data entry belongs to each cluster to a certain degree such as for example a likelihood of belonging to a cluster; for instance, and without limitation, a fuzzy clustering algorithm may be used to identify clustering of elements of a first type or category with elements of a second type or category, and vice versa, as described below. Cluster analysis may include strict partitioning clustering, whereby each observation or unclassified cluster data entry belongs to exactly one cluster. Cluster analysis may include strict partitioning clustering with outliers, whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering, whereby observations or unclassified cluster data entries that belong to a child cluster also belong to a parent cluster.

With continued reference to FIG. 1, computing device may generate a k-means clustering algorithm by receiving unclassified data and outputting a definite number of classified data entry clusters, wherein the data entry clusters each contain cluster data entries. K-means algorithm may select a specific number of groups or clusters to output, identified by a variable "k". Generating k-means clustering algorithm includes assigning inputs containing unclassified data to a "k-group" or "k-cluster" based on feature similarity. Centroids of k-groups or k-clusters may be utilized to generate classified data entry cluster. K-means clustering algorithm may select and/or be provided "k" variable by calculating k-means clustering algorithm for a range of k values and comparing results. K-means clustering algorithm may compare results across different values of k as the mean distance between cluster data entries and cluster centroid. K-means clustering algorithm may calculate mean distance to a centroid as a function of k value, and the location of where the rate of decrease starts to sharply shift, which may be utilized to select a k value. Centroids of k-groups or k-cluster include a collection of feature values which are utilized to classify data entry clusters containing cluster data entries. K-means clustering algorithm may act to identify clusters of closely related data, which may be provided with user cohort labels; this may, for instance, generate an initial set of user cohort labels from an initial set of data, and may also, upon subsequent iterations, identify new clusters to be provided new labels, to which additional data may be classified, or to which previously used data may be reclassified.

With continued reference to FIG. 1, generating a k-means clustering algorithm may include generating initial estimates for k centroids which may be randomly generated or randomly selected from unclassified data input. K centroids may be utilized to define one or more clusters. K-means clustering algorithm may assign unclassified data to one or more k-centroids based on the squared Euclidean distance by first performing a data assigned step of unclassified data. K-means clustering algorithm may assign unclassified data to its nearest centroid based on the collection of centroids ci of centroids in set C. Unclassified data may be assigned to a cluster based on $\text{argmin}_{c_i \ni C} \text{dist}(c_i, x)^2$, where argmin includes argument of the minimum, ci includes a collection of centroids in a set C, and dist includes standard Euclidean distance. K-means clustering module may then recompute centroids by taking a mean of all cluster data entries assigned to a centroid's cluster. This may be calculated based on $c_i = 1/|S_i| \Sigma x_i \ni S_i^{x_i}$. K-means clustering algorithm may continue to repeat these calculations until a stopping criterion has been satisfied such as when cluster data entries do not change clusters, the sum of the distances have been minimized, and/or some maximum number of iterations has been reached.

With continued reference to FIG. 1, k-means clustering algorithm may be configured to calculate a degree of similarity index value. For the purposes of this disclosure, a "degree of similarity index value" is a distance measured between each data entry cluster generated by k-means clustering algorithm and a selected element. Degree of similarity index value may indicate how close a particular combination of elements is to being classified by k-means algorithm to a particular cluster. K-means clustering algorithm may evaluate the distances of the combination of elements to the k-number of clusters output by k-means clustering algorithm. Short distances between an element of data and a cluster may indicate a higher degree of similarity between the element of data and a particular cluster. Longer distances between an element and a cluster may indicate a lower degree of similarity between the element to be compared and/or clustered and a particular cluster.

With continued reference to FIG. 1, k-means clustering algorithm selects a classified data entry cluster as a function of the degree of similarity index value. In one or more embodiments, k-means clustering algorithm may select a classified data entry cluster with the smallest degree of similarity index value indicating a high degree of similarity between an element and the data entry cluster. Alternatively and/or additionally, k-means clustering algorithm may select a plurality of clusters having low degree of similarity index values to elements to be compared and/or clustered thereto, indicative of greater degrees of similarity. Degree of similarity index values may be compared to a threshold number indicating a minimal degree of relatedness suitable for inclusion of a set of element data in a cluster, where degree of similarity indices a-n falling under the threshold number may be included as indicative of high degrees of relatedness. The above-described illustration of feature learning using k-means clustering is included for illustrative purposes only and should not be construed as limiting potential implementation of feature learning algorithms; a person of ordinary skills in the art, upon reviewing the entirety of this disclosure, will be aware of various additional or alternative feature learning approaches, such as particle swarm optimization (PSO) and generative adversarial network (GAN) that may be used consistently with this disclosure.

With continued reference to FIG. 1, in one or more embodiments, processor 132 may use an image recognition algorithm to determine patterns within an image. In one or more embodiments, image recognition algorithm may include an edge-detection algorithm, which may detect one or more shapes defined by edges. For the purposes of this disclosure, an "edge detection algorithm" is or includes a mathematical method that identifies points in a digital image at which the image brightness changes sharply and/or has discontinuities. In one or more embodiments, such points may be organized into straight and/or curved line segments, which may be referred to as "edges". Edge detection may be performed using any suitable edge detection algorithm, including without limitation Canny edge detection, Sobel operator edge detection, Prewitt operator edge detection, Laplacian operator edge detection, and/or differential edge detection. Edge detection may include phase congruency-based edge detection, which finds all locations of an image where all sinusoids in the frequency domain, for instance when generated using a Fourier decomposition, may have matching phases which may indicate a location of an edge.

With continued reference to FIG. 1, processor 132 is configured to receive, from ultrasonic imaging system 104, at least a query image 108, and identify a pose 144 of an anatomical structure as a function of the at least a query image 108. For the purposes of this disclosure, a "pose" is a set of geometric parameters that collectively describe the location and orientation of an object with respect to the position of image capture device or vice versa. For the purposes of this disclosure, an "anatomical structure" is an organ, a tissue, or a portion thereof that is capable of being analyzed by apparatus 100 for medically relevant information. Anatomical structure may include any type of tissue, organ, or the like to which apparatus 100 may be applicable, as recognized by a person of ordinary skill in the art upon reviewing the entirety of this disclosure. Nonlimiting examples of anatomical structure may include at least a portion of a heart, a liver, a lung, a kidney, a thyroid, a prostate, a uterus, or the like, consistent with details described above. In one or more embodiments, identifying pose 144 of an anatomical structure may include locating at least a point of view (POV) 144a as a function of query image 108 and determining a view angle (VA) 144b as a function of the at least a POV 144a, wherein the at least a POV 144a and the VA 144b define at least a portion the anatomical structure. Portion of anatomical structure may include a portion of the heart, such as the left atrium. For the purposes of this disclosure, a "point of view (POV)" is a specific spatial location or origin from which an image or scene is observed or captured. For the purposes of this disclosure, a "view angle (VA)" is an angular orientation or direction defined by one or more θ and φ angles that is projected from POV 144a. In some embodiments, VA may be expressed using cylindrical coordinates. In some embodiments, VA may be expressed in spherical coordinates. In some cases, identifying pose 144 of anatomical structure may include retrieving a 3D model or creating a 3D model from plurality of images to position query image 108 therein. 3D model may include a 3D heart model. As a nonlimiting example, 3D model/3D heart model may be created using a statistical shape model (SSM). For the purposes of this disclosure, a statistical shape model (SSM) is a mathematical representation of the shape variations within a collection of objects. SSM uses statistical methods to capture the common features and variations of shapes in a dataset. SSM is often applied in fields such as medical imaging, computer vision, and biomechanics. In some cases, construction of SSM may include a principal component analysis (PCA). For the purposes of this disclosure, principal component analysis (PCA) is a dimensionality reduction technique used to identify the main axes of variation in the data. In the context of SSM, PCA may be applied to coordinates of landmark points on the shapes to find these principal components, which are also known as modes of variation. Construction of SSM may include converting a plurality of pixels to a set of statistical shape eigenvalues. As a nonlimiting example, when PCA is performed on a set of shape data, it may result in a set of eigenvalues and eigenvectors. These eigenvalues may represent the amount of variance captured by each principal component (eigenvector). Each eigenvalue in an SSM may indicate how much of the total shape variation is explained by the corresponding principal component. As a nonlimiting example, larger eigenvalues may indicate that its corresponding principal component captures more of the shape variation in the dataset; accordingly, components with small eigenvalues may contribute little to the overall variance and can often be excluded to simplify the model without losing significant information. If a first eigenvalue is significantly larger than the others, it means the first principal component accounts for most of the shape variation. By examining these eigenvalues, one can decide how many principal components are needed to adequately describe the shape variation. These eigenvalues, together with the corresponding eigenvectors, may be used to reconstruct shapes from a model. A shape may be approximated as a mean shape plus a weighted sum of the principal components, wherein the weights are determined by these eigenvalues. As a nonlimiting example, in a medical imaging context, PCA may be applied to a dataset pertaining to a 3D heart model, and accordingly, one might find that the first few eigenvalues are large, indicating that the main variations in heart shape may be described with a few principal components. These eigenvalues may be helpful in understanding major modes of shape variation, such as changes in size or specific anatomical features, which may be crucial for diagnosis and treatment planning. Details regarding the determination of pose 144, POV 144a, and VA 144b, generation of 3D model, overlaying one or more images within such 3D model, as well as any function or functions related thereto, may be consistent with any detail disclosed in U.S. patent application Ser. No. 18/376,688, filed on Oct. 4, 2023, and entitled "APPARATUS AND METHODS FOR GENERATING A THREE-DIMENSIONAL (3D) MODEL OF CARDIAC ANATOMY VIA MACHINE-LEARNING", U.S. patent application Ser. No. 18/509,520, filed on Nov. 15, 2023, and entitled "APPARATUS AND METHODS FOR SYNTHETIZING MEDICAL IMAGES", U.S. patent application Ser. No. 18/395,087, filed on Dec. 22, 2023, and entitled "APPARATUS AND METHOD FOR GENERATING A THREE-DIMENSIONAL (3D) MODEL OF CARDIAC ANATOMY WITH AN OVERLAY", and U.S. patent application Ser. No. 18/648,176, filed on Apr. 26, 2024, and entitled "APPARATUS AND METHODS FOR VISUALIZATION WITHIN A THREE-DIMENSIONAL MODEL USING NEURAL NETWORKS", the entirety of each of which is incorporated herein by reference.

With continued reference to FIG. 1, processor 132 is configured to determine at least a medical feature 148 as a function of pose 144 of anatomical structure. Medical feature 148 may include any type of structural, biological, physiological, or biomedical features or functions related to an anatomical structure of a patient and/or pertinent to concurrent medical procedure 116. Exemplary medical features 148 may include, without limitation, a case of calcification 152 at a heart valve, a thrombus 156 in the left atrial appendage, one or more abnormal heart valve movements or functions 160, and a thickness 164 including a heart wall thickness 164, among others. For the purposes of this disclosure, "calcification" is a condition in which calcium deposits form on a heart valve. As a nonlimiting example, a human heart contains four heart valves: the mitral valve located between the left atrium and the left ventricle, the aortic valve located between the left ventricle and the aorta, the tricuspid valve located between the right atrium and the right ventricle, and the pulmonary valve located between the right atrium and the pulmonary artery; calcification may occur at any of these locations with various likelihoods. These calcium deposits may cause the opening of a heart valve to become narrow. As a nonlimiting example, severe narrowing in the aortic valve may reduce the blood flow therethrough to result in a condition called aortic valve stenosis. In some cases, medical feature 148 may include one or more numerical or descriptive indicators that indicate a severity of calcification, such as "6/10" or "severe".

With continued reference to FIG. 1, for the purposes of this disclosure, a "thrombus in the left atrial appendage" is a blood clot in a small, ear-shaped outpouching of the muscular wall of the left atrium. Such a blood clot may expose a patient to an increased risk for cerebral stroke or peripheral embolism and may be treated using a left atrial appendage occlusion procedure. For the purposes of this disclosure, an "abnormal" heart valve movement or function is a type of heart valve movement or function associated with a minority of population and/or described by a numerical value that is different from a statistical average of the population, according to one or more cutoffs and/or predetermined criteria. As a nonlimiting example, an abnormal heart valve function 160 may be specified as a heart valve function possessed by or associated with less than 10% of the population and/or described by a numerical value that is at least two standard deviations away from statistical average. Exemplary abnormal heart valve functions 160 may include cases such as regurgitation (i.e., a case with a backward flow of blood due to a heart valve not closing properly), stenosis (i.e., a case where a heart valve's leaflets thicken, stiffen, or stick together), and atresia (i.e., a case with one or more heart valves missing). For the purposes of this disclosure, a "heart valve movement" or "heart valve function" is a movement or function performed by a heart valve in order to regulate a blood flow. Exemplary heart valve movements or functions may include a direction towards which a heart valve may open, an extent to which a heart valve may open or close, among others, consistent with details described above. In some cases, medical feature 148 may include one or more numerical or descriptive indicators that indicate a general assessment of a heart valve movement or function and/or a severity of one or more abnormal heart valve movements or functions, such as "95/100" or "mild".

With continued reference to FIG. 1, for the purposes of this disclosure, a "thickness" is a radial distance, from an interior surface of an organ or tissue to an exterior surface of the organ or tissue, that measures the thickness of the structure in between. For the purposes of this disclosure, a "heart wall thickness" is a thickness pertaining to the muscle of a heart wall. Thickness 164 such as heart wall thickness 164 may vary from one individual to another, and different locations of an anatomical structure may have different thicknesses. Thickness 164 may be a relevant parameter to factor in while performing concurrent medical procedure 116. As a nonlimiting example, for a cardiac ablation procedure, a lower power, a smaller amount of energy, and/or a shorter duration of operation may be applied to one part of a heart wall with a smaller heart wall thickness 164, whereas a higher power, a larger amount of energy, and/or a longer duration of operation may be applied to another part of a heart wall with a larger heart wall thickness 164. Additional details will be provided below.

With continued reference to FIG. 1, determining at least a medical feature 148 comprises receiving feature training data 168 comprising a plurality of training images as input and a plurality of labelled features as output. For the purposes of this disclosure, a "training image" is an image that may be used to train a machine learning algorithm or model. In one or more embodiments, feature training data 168 may include data specifically synthesized for training purposes using one or more generative models, as described in this disclosure. As a nonlimiting example, feature training data 168, training images, and/or plurality of labelled features may be extracted from medical literature, which may be in consistence with any detail disclosed in U.S. patent application Ser. No. 18/648,059, filed on Apr. 26, 2024, and entitled "APPARATUS AND METHODS FOR GENERATING DIAGNOSTIC HYPOTHESES BASED ON BIOMEDICAL SIGNAL DATA", the entirety of which is incorporated herein by reference. In one or more embodiments, one or more query images 108 may be incorporated into feature training data 168 upon validation by users such as medical professionals. In one or more embodiments, feature training data 168 may be retrieved from one or more databases 140, EHRs, and/or other repositories of similar nature, or be supplied as one or more user inputs. In one or more embodiments, at least a portion of feature training data 168 may be added, deleted, replaced, or otherwise updated as a function of one or more inputs from one or more users.

With continued reference to FIG. 1, in one or more embodiments, plurality of labelled features may include a presence or absence of calcification 152 at one or more heart valves. In one or more embodiments, plurality of labelled features may include a presence or absence of thrombus 156 in the left atrial appendage of a heart. In one or more embodiments, plurality of labelled features may include a plurality of heart valve functions 160. In one or more embodiments, plurality of labelled features may include a plurality of thicknesses 164 such as heart wall thicknesses 164.

With continued reference to FIG. 1, determining at least a medical feature 148 further comprises training an image processing machine learning model 172 comprising a plurality of image processing algorithms 176 using feature training data 168. For the purposes of this disclosure, an "image processing machine learning model" is a data structure capable of processing at least a query image 108 and/or training image and extracting one or more features therefrom. In some cases, image processing machine learning model 172 may include a generative model and/or otherwise implement one or more types of artificial intelligence (AI) algorithms in consistence with any type of machine learning model or algorithm described herein that's deemed suitable by a person of ordinary skill in the art upon reviewing the entirety of this disclosure. For the purposes of this disclosure, a "data structure" is a format of data organization, management, and storage that is usually chosen for efficient access to data. Image processing machine learning model 172 may include any type of data structure recognized by a person of ordinary skill in the art upon reviewing the entirety of this disclosure, such as without limitation, stack, queue, array, list, or tree.

With continued reference to FIG. 1, determining at least a medical feature 148 further comprises determining at least a medical feature 148 as a function of at least a query image 108 using the trained image processing machine learning model 172. It is worth noting that plurality of image processing algorithms 176 may adopt a hierarchical structure and/or be implemented across a variety of functions of apparatus 100. In one or more embodiments, identifying pose 144 of the heart may include locating at least a POV 144a as a function of query image 108 and a first subset of plurality of image processing algorithms 176, consistent with details described above. In such embodiments, determining at least a medical feature 148 may include determining the at least a medical feature 148 as a function of a second subset of plurality of image processing algorithms 176. As a nonlimiting example, first subset of plurality of image processing algorithms 176 may be trained using at least a portion of feature training data 168 that contain a plurality of poses 144, POVs 144a, and/or VA 144b correlated with a collection of ICEs. Accordingly, first subset of plurality of image processing algorithms 176, once trained, may use query image 108 (e.g., a query ICE) to identify a match from this collection of ICEs and identify a set of pose 144, POV 144a, and VA 144b associated with the match. Identification of such a match may involve, for example and without limitation, comparing a first set of neural network encodings extracted from query image 108 with at least a second set of neural network encodings extracted from each ICE of the collection of ICEs. For the purposes of this disclosure, "neural network encodings" are a plurality of parameters extracted by one or more neural networks that collectively describe features of a system and/or connections between elements therein. Neural network encodings may include weights/biases/coefficients of neural network nodes, embeddings (vectors) generated by the neural networks, or a combination thereof, consistent with details described below in this disclosure. Details described herein may be consistent with any detail disclosed in U.S. patent application Ser. No. 18/395,087, filed on Dec. 22, 2023, and entitled "APPARATUS AND METHOD FOR GENERATING A THREE-DIMENSIONAL (3D) MODEL OF CARDIAC ANATOMY WITH AN OVERLAY", and U.S. patent application Ser. No. 18/648,176, filed on Apr. 26, 2024, and entitled "APPARATUS AND METHODS FOR VISUALIZATION WITHIN A THREE-DIMENSIONAL MODEL USING NEURAL NETWORKS", the entirety of each of which is incorporated herein by reference.

With continued reference to FIG. 1, in one or more embodiments, determining at least a medical feature 148 may include identifying a thrombus 156 in the left atrial appendage of the heart, consistent with details described above. In one or more embodiments, determining at least a medical feature 148 may include identifying case of calcification 152 in a heart valve consistent with details described above. In one or more embodiments wherein plurality of labelled features includes plurality of heart valve functions, determining at least a medical feature 148 may include classifying feature training data 168 into a plurality of classes 180, using a classifier 184 including any suitable type of classifier described in this disclosure, as a function of the plurality of heart valve functions, wherein each class 180 of the plurality of classes 180 shares at least one similar heart valve function, and classifying an abnormal heart valve function 160 (e.g., based on its severity) as a function of the plurality of classes 180, consistent with details described in the rest of this disclosure. As a nonlimiting example, an abnormal heart valve function may be classified as "mild", "intermediate", or "severe".

With continued reference to FIG. 1, in one or more embodiments wherein plurality of labelled features includes plurality of thicknesses 164, such as a plurality of heart wall thicknesses 164. Accordingly, determining at least a medical feature 148 may include determining thickness 164 such as heart wall thickness 164. In such cases, determining at least a medical feature 148 may include labeling, using a labeling algorithm 188, feature training data 168 with a plurality of labels 192 as a function of plurality of thicknesses 164, wherein each label 192 of the plurality of labels shares a similar thickness 164, and determining thickness 164 as a function of the plurality of labels 192. For the purposes of this disclosure, a "labeling algorithm" is a mathematical algorithm or model configured to perform one or more labeling functions or creating one or more labels 192. For the purposes of this disclosure, "labeling" is a process of identifying raw data such as feature training data 168 and adding one or more meaningful and informative labels 192 to provide a context for one or more following steps. For the purposes of this disclosure, a "label" is an indication describing one or more characteristics of a subject matter (e.g., one or more medical features 148) as well as how the subject matter may be categorized into one or more categories with respect to a population or sub-population containing the subject. In one or more embodiments, label 192 may include a binary label, e.g., "normal" vs. "abnormal" or "included" vs. "not included". In one or more embodiments, label 192 may be further specified, such as "abnormally thick" or "abnormally thin". In one or more embodiments, label 192 may be associated with a percentile ranking, e.g., "top 10% of the population by heart wall thickness". In one or more embodiments, label 192 may be applied with respect to at least a specific cohort upon application of one or more inclusion/exclusion criteria, such as "top 25% of the female population by heart wall thickness".

With continued reference to FIG. 1, labeling feature training data 168 may include analyzing statistical distribution of thicknesses 164. For the purposes of this disclosure, a "statistical distribution" or "statistical model" is a mathematical model that describes a plurality of data elements collectively as a group. Statistical distribution may include one or more numerical indicators such as without limitation an average or mean, a median, a standard deviation, a variance, a range, or the like. Additionally and/or alternatively, statistical distribution may include characteristics or metrics that describe how one data element or group of data elements compares to another data element or group of data elements. In some cases, a match between a first set of statistical metrics and a second set of statistical metrics may be determined as a function of one or more pre-determined criteria selected by one or more medical professionals. As a nonlimiting example, a first set of statistical metrics and a second set of statistical metrics may be considered a match when the two sets of statistical metrics are within one standard deviation from each other. As another nonlimiting example, matching a first set of statistical metrics with a second set of statistical metrics may involve a fuzzy set comparison, as described below. As another nonlimiting example, determining the heart wall thickness may include determining the heart wall thickness as an outlier based on statistical distribution, as described above.

With continued reference to FIG. 1, processor 132 is further configured to suggest, using display device 128, a modification 196a-d to concurrent medical procedure 116 as a function of the at least a medical feature 148. For the purposes of this disclosure, a "modification" is an action proposed to correct or change one or more aspects of concurrent medical procedure 116 in order to improve its outcome. In some cases, such modification 196a-d may be automated or semi-automated, under an autopilot or a semi-autopilot mode, that requires limited human intervention. In one or more embodiments wherein determining at least a medical feature 148 includes identifying a case of calcification 152 in a heart valve, suggesting modification 196a to concurrent medical procedure 116 may include avoiding, using catheter 120, the heart valve upon identifying the case of calcification 152. In one or more embodiments wherein determining at least a medical feature 148 includes identifying a thrombus 156 in the left atrial appendage of the heart, as described above, suggesting modification 196b-c to concurrent medical procedure 116 may include terminating or adjusting ablation procedure 124 upon identifying the thrombus 156 and/or abnormal heart valve function 160. In one or more embodiments, suggesting modification 196d to concurrent medical procedure 116 may include adjusting at least a parameter of ablation procedure 124 as a function of thickness 164 as described above. Exemplary parameters of ablation procedure 124 may include without limitation voltage, pulse duration, frequency, pulse width, amplitude, power of ablation, total energy delivered, total treatment time, energy delivered to a particular location, treatment time at a particular location, current, average power, peak power, and biphasic vs monophasic pulse delivery, among others.

With continued reference to FIG. 1, it should be noted that apparatus 100 and related methods described herein are not limited to heart-related applications only. For example, and without limitation, apparatus 100 may be used to provide real-time navigation for medical procedures performed on organs such as livers, lungs, kidneys, thyroids, prostates, uteruses, or the like, where precision and minimally invasive diagnostics and/or treatments are also crucial. A person of ordinary skill in the art, upon reviewing the entirety of this disclosure, will recognize one or more embodiments described herein (although principally focused on the heart) and their underlaying principles may be readily transferrable to a broader context of medical imaging and intervention applications that is not currently disclosed.

Figure 2:
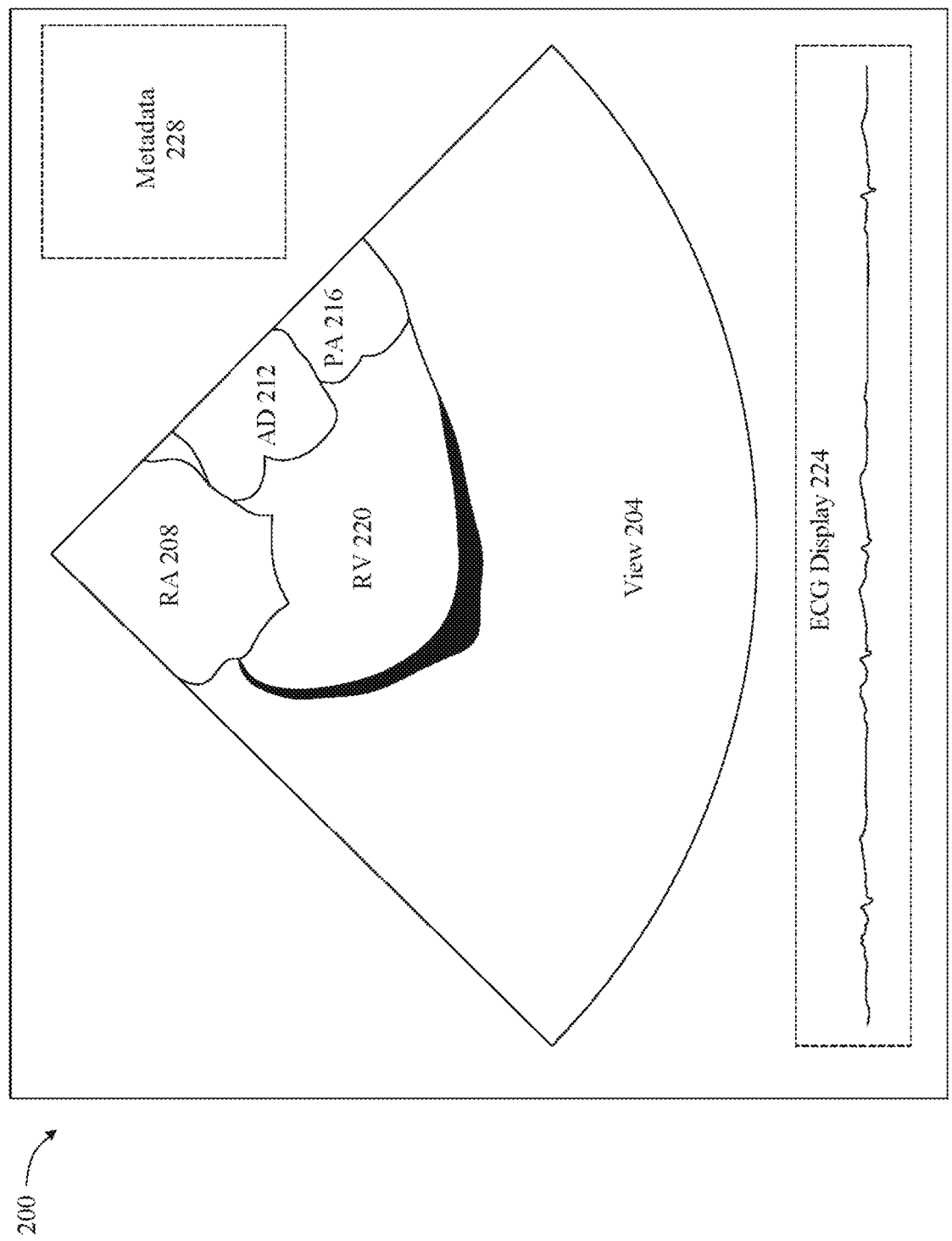
FIG. 2 is an illustration of an exemplary embodiment of ultrasound data.

Referring now to FIG. 2, an exemplary embodiment of ultrasound data 200 is illustrated. In one or more embodiments, ultrasound data 200 may include an ICE, consistent with details described above. ICE may be a real-time, dynamic ultrasound image that provides a view 204 of heart's interior structures, including, without limitation, right atrium (RA) 208, anterior descending (AD) 212, pulmonary atresia (PA) 216, and right ventricular (RV) 220.

With continued reference to FIG. 2, in one or more embodiments, ICE may include a grayscale image. It should be noted that, in one or more embodiments, ICE may be configured to visualize blood flow and/or blood flow patterns within a heart via color doppler. In one or more embodiments, resolution and/or clarity of ICE may be superior to TTE or TEE due to the fact that catheter 120 may be positioned inside a heart, closer to the structures being imaged.

With continued reference to FIG. 2, in a nonlimiting example, heart chambers may appear as dark, anechoic (black) areas since they are filled with blood, which doesn't reflect ultrasound waves well. Heart walls, valves, and/or other structures may appear as varying shades of gray, depending on their density and composition. In one or more embodiments, color doppler overlays may show blood flow in different colors, indicating the direction and speed of blood flow. For instance, and without limitation, red may indicate flow towards the probe, whereas blue may indicate flow away from the probe.

With continued reference to FIG. 2, in one or more embodiments, ICE may be synchronized with an electrocardiogram (ECG), allowing for precise timing of cardiac events with anatomical visualization provided by ICE. For the purposes of this disclosure, an "electrocardiogram (ECG)" is a recording of electrical activity of a patient's heart over a period of time. In one or more embodiments, ICE may include an ECG display 224 configured to display ECG waveform as a continuous line graph. In one or more embodiments, specific parts of the cardiac cycle, e.g., systole or diastole, may be correlated and/or synchronized with visual data from ICE.

With continued reference to FIG. 2, Additionally and/or alternatively, ICE may be accompanied by metadata 228 displayed on the side or corners of ICE as described herein. In one or more embodiments, metadata 228 may provide essential contextual information about ICE and/or the corresponding patient. In a nonlimiting example, metadata 228 may include patient information (e.g., patient ID, name, DOB, age, gender, and the like), image acquisition details (e.g., date and time, probe type, frequency, depth, gain, and the like), procedure-related information (e.g., procedure name, operator, location, and the like), ECG data, measurement annotations (e.g., any measurements taken directly on the image e.g., diameter, a value of thickness of a heart wall, and the like), image sequence information (e.g., image number, total number of frames, and the like), comments or notes, hospital or clinic information, and/or the like. A person of ordinary skill in the art, upon reviewing the entirety of this disclosure, will be aware of how ICE and various components thereof may be incorporated within apparatus 100 in order for it to perform one or more of its functions.

Figure 3:
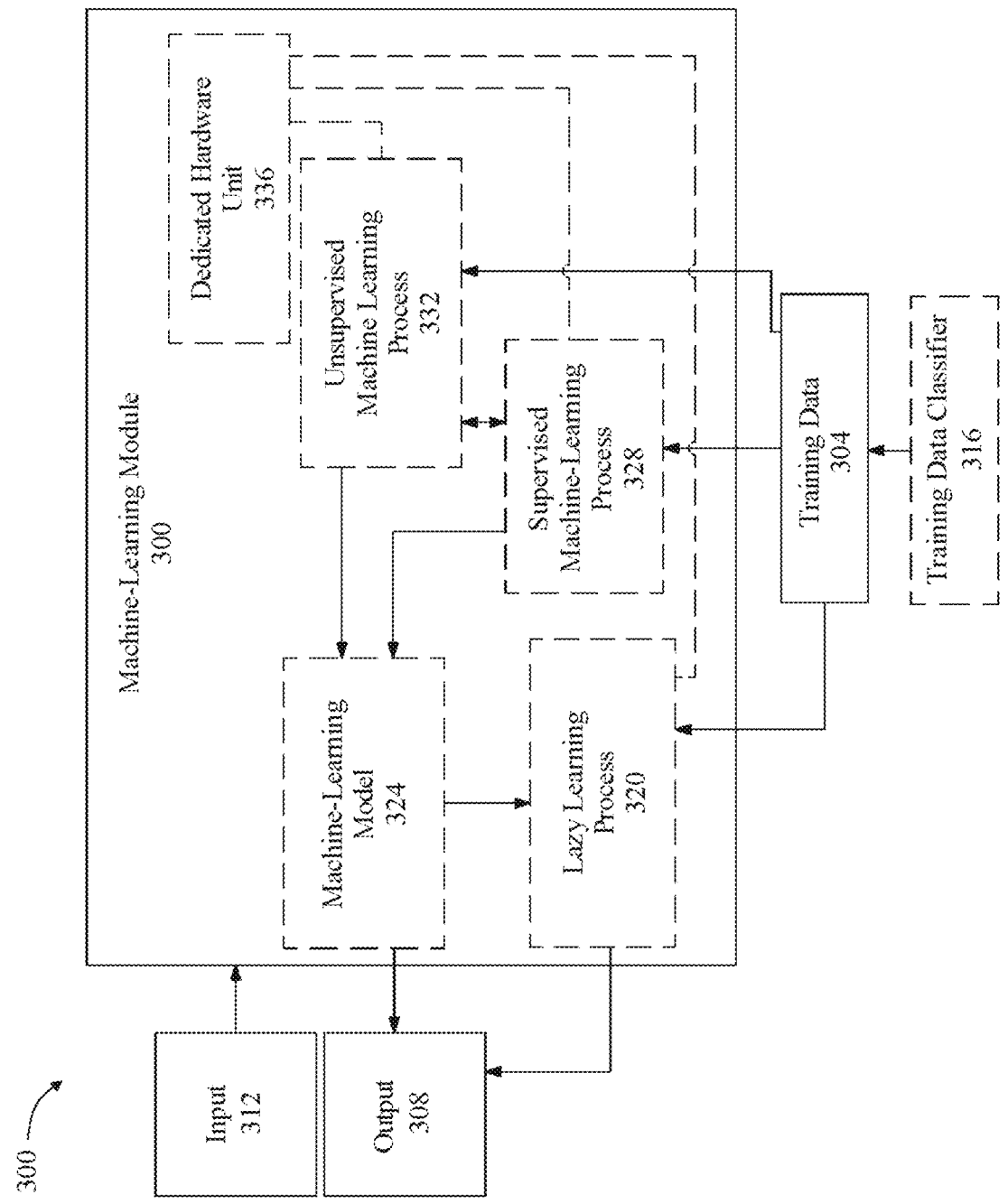
FIG. 3 is a block diagram of an exemplary embodiment of a machine learning module.

Referring now to FIG. 3, an exemplary embodiment of a machine learning module 300 that may perform one or more machine learning processes as described above is illustrated. Machine learning module may perform determinations, classification, and/or analysis steps, methods, processes, or the like as described in this disclosure using machine learning processes. For the purposes of this disclosure, a "machine learning process" is an automated process that uses training data 304 to generate an algorithm instantiated in hardware or software logic, data structures, and/or functions that will be performed by a computing device/module to produce outputs 308 given data provided as inputs 312; this is in contrast to a non-machine learning software program where the commands to be executed are pre-determined by user and written in a programming language.

With continued reference to FIG. 3, "training data", for the purposes of this disclosure, are data containing correlations that a machine learning process may use to model relationships between two or more categories of data elements. For instance, and without limitation, training data 304 may include a plurality of data entries, also known as "training examples", each entry representing a set of data elements that were recorded, received, and/or generated together. Data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine learning processes as described in further detail below. Training data 304 may be formatted and/or organized by categories of data elements, for instance by associating data elements with one or more descriptors corresponding to categories of data elements. As a nonlimiting example, training data 304 may include data entered in standardized forms by persons or processes, such that entry of a given data element within a given field in a given form may be mapped to one or more descriptors of categories. Elements in training data 304 may be linked to descriptors of categories by tags, tokens, or other data elements. For instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

With continued reference to FIG. 3, Alternatively and/or additionally, training data 304 may include one or more elements that are uncategorized; that is, training data 304 may not be formatted or contain descriptors for some elements of data. Machine learning algorithms and/or other processes may sort training data 304 according to one or more categorizations using, for instance, natural language processing algorithms, tokenization, detection of correlated values in raw data, and the like; categories may be generated using correlation and/or other processing algorithms. As a nonlimiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine learning algorithms, and/or automated association of data in the data entry with descriptors or into a given format. The ability to categorize data entries automatedly may enable the same training data 304 to be made applicable for two or more distinct machine learning algorithms as described in further detail below. Training data 304 used by machine learning module 300 may correlate any input data as described in this disclosure to any output data as described in this disclosure. As a nonlimiting illustrative example, inputs may include plurality of ultrasound images, whereas outputs may include plurality of medical features 148.

With continued reference to FIG. 3, training data 304 may be filtered, sorted, and/or selected using one or more supervised and/or unsupervised machine learning processes and/or models as described in further detail below; such processes and/or models may include without limitation a training data classifier 316. For the purposes of this disclosure, a "classifier" is a machine learning model, such as a data structure representing and/or using a mathematical model, neural net, or a program generated by a machine learning algorithm, known as a "classification algorithm", that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine learning module 300 may generate a classifier using a classification algorithm. For the purposes of this disclosure, a "classification algorithm" is a process wherein a computing device and/or any module and/or component operating therein derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, Fisher's linear discriminant, quadratic classifiers, decision trees, boosted trees, random forest classifiers, learning vector quantization, and/or neural network-based classifiers. In one or more embodiments, training data classifier 316 may classify elements of training data to a plurality of cohorts as a function of certain anatomic and/or demographic traits.

With continued reference to FIG. 3, machine learning module 300 may be configured to generate a classifier using a naive Bayes classification algorithm. Naive Bayes classification algorithm generates classifiers by assigning class labels to problem instances, represented as vectors of element values. Class labels are drawn from a finite set. Naive Bayes classification algorithm may include generating a family of algorithms that assume that the value of a particular element is independent of the value of any other element, given a class variable. Naive Bayes classification algorithm may be based on Bayes Theorem expressed as P(A/B)=P(B/A)×P(A)÷P(B), where P(A/B) is the probability of hypothesis A given data B, also known as posterior probability; P(B/A) is the probability of data B given that the hypothesis A was true; P(A) is the probability of hypothesis A being true regardless of data, also known as prior probability of A; and P(B) is the probability of the data regardless of the hypothesis. A naive Bayes algorithm may be generated by first transforming training data into a frequency table. Machine learning module 300 may then calculate a likelihood table by calculating probabilities of different data entries and classification labels. Machine learning module 300 may utilize a naive Bayes equation to calculate a posterior probability for each class. A class containing the highest posterior probability is the outcome of prediction. Naive Bayes classification algorithm may include a gaussian model that follows a normal distribution. Naive Bayes classification algorithm may include a multinomial model that is used for discrete counts. Naive Bayes classification algorithm may include a Bernoulli model that may be utilized when vectors are binary.

With continued reference to FIG. 3, machine learning module 300 may be configured to generate a classifier using a k-nearest neighbors (KNN) algorithm. For the purposes of this disclosure, a "k-nearest neighbors algorithm" is or at least includes a classification method that utilizes feature similarity to analyze how closely out-of-sample features resemble training data 304 and to classify input data to one or more clusters and/or categories of features as represented in training data 304; this may be performed by representing both training data 304 and input data in vector forms and using one or more measures of vector similarity to identify classifications within training data 304 and determine a classification of input data. K-nearest neighbors algorithm may include specifying a k-value, or a number directing the classifier to select the k most similar entries of training data 304 to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a nonlimiting example, an initial heuristic may include a ranking of associations between inputs 312 and elements of training data 304. Heuristic may include selecting some number of highest-ranking associations and/or training data elements.

With continued reference to FIG. 3, generating k-nearest neighbors algorithm may generate a first vector output containing a data entry cluster, generating a second vector output containing input data, and calculate the distance between the first vector output and the second vector output using any suitable norm such as cosine similarity, Euclidean distance measurement, or the like. Each vector output may be represented, without limitation, as an n-tuple of values, where n is at least 2. Each value of n-tuple of values may represent a measurement or other quantitative value associated with a given category of data or attribute, examples of which are provided in further detail below. A vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent when their directions and/or relative quantities of values are the same; thus, as a nonlimiting example, a vector represented as [5, 10, 15] may be treated as equivalent, for the purposes of this disclosure, as a vector represented as [1, 2, 3]. Vectors may be more similar where their directions are more similar, and more different where their directions are more divergent. However, vector similarity may Alternatively and/or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized", or divided by a "length" attribute, such as a length attribute 1 as derived using a Pythagorean norm:

$$l = \sqrt{\sum_{i=0}^{n} a_i^2},$$

where $a_i$ is attribute number of vector i. Scaling and/or normalization may function to make vector comparison independent of absolute quantities of attributes, while preserving any dependency on similarity of attributes. This may, for instance, be advantageous where cases represented in training data 304 are represented by different quantities of samples, which may result in proportionally equivalent vectors with divergent values.

With continued reference to FIG. 3, training examples for use as training data may be selected from a population of potential examples according to cohorts relevant to an analytical problem to be solved, a classification task, or the like. Alternatively and/or additionally, training data 304 may be selected to span a set of likely circumstances or inputs for a machine learning model and/or process to encounter when deployed. For instance, and without limitation, for each category of input data to a machine learning model and/or process that may exist in a range of values in a population of phenomena such as images, user data, process data, physical data, or the like, a computing device, processor 132, and/or machine learning module 300 may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively and/or additionally, a set of training examples may be compared to a collection of representative values in a database and/or presented to user, so that a process can detect, automatically or via user input, one or more values that are not included in the set of training examples. Computing device, processor 132, and/or machine learning module 300 may automatically generate a missing training example. This may be done by receiving and/or retrieving a missing input and/or output value and correlating the missing input and/or output value with a corresponding output and/or input value collocated in a data record with the retrieved value, provided by user, another device, or the like.

With continued reference to FIG. 3, computing device, processor 132, and/or machine learning module 300 may be configured to preprocess training data 304. For the purposes of this disclosure, "preprocessing" training data is a process that transforms training data from a raw form to a format that can be used for training a machine learning model. Preprocessing may include sanitizing, feature selection, feature scaling, data augmentation and the like.

With continued reference to FIG. 3, computing device, processor 132, and/or machine learning module 300 may be configured to sanitize training data. For the purposes of this disclosure, "sanitizing" training data is a process whereby training examples that interfere with convergence of a machine learning model and/or process are removed to yield a useful result. For instance, and without limitation, a training example may include an input and/or output value that is an outlier from typically encountered values, such that a machine learning algorithm using the training example will be skewed to an unlikely range of input 312 and/or output 308; a value that is more than a threshold number of standard deviations away from an average, mean, or expected value, for instance, may be eliminated. Alternatively and/or additionally, one or more training examples may be identified as having poor-quality data, where "poor-quality" means having a signal-to-noise ratio below a threshold value. In one or more embodiments, sanitizing training data may include steps such as removing duplicative or otherwise redundant data, interpolating missing data, correcting data errors, standardizing data, identifying outliers, and/or the like. In one or more embodiments, sanitizing training data may include algorithms that identify duplicate entries or spell-check algorithms.

With continued reference to FIG. 3, in one or more embodiments, images used to train an image classifier or other machine learning model and/or process that takes images as inputs 312 or generates images as outputs 308 may be rejected if image quality is below a threshold value. For instance, and without limitation, computing device, processor 132, and/or machine learning module 300 may perform blur detection. Elimination of one or more blurs may be performed, as a nonlimiting example, by taking Fourier transform or a Fast Fourier Transform (FFT) of image and analyzing a distribution of low and high frequencies in the resulting frequency-domain depiction of the image. Numbers of high-frequency values below a threshold level may indicate blurriness. As a further nonlimiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of image, based on the hypothesis that rapid changes indicate sharp edges in the image, and thus are indicative of a lower degree of blurriness. Blur detection may be performed using a wavelet-based operator, which uses coefficients of a discrete wavelet transform to describe the frequency and spatial content of images. Blur detection may be performed using statistics-based operators that take advantage of several image statistics as texture descriptors in order to compute a focus level. Blur detection may be performed by using discrete cosine transform (DCT) coefficients in order to compute a focus level of an image from its frequency content.

With continued reference to FIG. 3, computing device, processor 132, and/or machine learning module 300 may be configured to precondition one or more training examples. For instance, and without limitation, where a machine learning model and/or process has one or more inputs 312 and/or outputs 308 requiring, transmitting, or receiving a certain number of bits, samples, or other units of data, one or more elements of training examples to be used as or compared to inputs 312 and/or outputs 308 may be modified to have such a number of units of data. In one or more embodiments, computing device, processor 132, and/or machine learning module 300 may convert a smaller number of units, such as in a low pixel count image, into a desired number of units by upsampling and interpolating. As a nonlimiting example, a low pixel count image may have 100 pixels, whereas a desired number of pixels may be 128. Processor 132 may interpolate the low pixel count image to convert 100 pixels into 128 pixels. It should also be noted that one of ordinary skill in the art, upon reading the entirety of this disclosure, would recognize the various methods to interpolate a smaller number of data units such as samples, pixels, bits, or the like to a desired number of such units. In one or more embodiments, a set of interpolation rules may be trained by sets of highly detailed inputs 312 and/or outputs 308 and corresponding inputs 312 and/or outputs 308 downsampled to smaller numbers of units, and a neural network or another machine learning model that is trained to predict interpolated pixel values using the training data 304. As a nonlimiting example, a sample input 312 and/or output 308, such as a sample picture, with sample-expanded data units (e.g., pixels added between the original pixels) may be input to a neural network or machine learning model and output a pseudo replica sample picture with dummy values assigned to pixels between the original pixels based on a set of interpolation rules. As a nonlimiting example, in the context of an image classifier, a machine learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively and/or additionally, computing device, processor 132, and/or machine learning module 300 may utilize sample expander methods, a low-pass filter, or both. For the purposes of this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor 132, and/or machine learning module 300 may use averaging, such as luma or chroma averaging in images, to fill in data units in between original data units.

With continued reference to FIG. 3, in one or more embodiments, computing device, processor 132, and/or machine learning module 300 may downsample elements of a training example to a desired lower number of data elements. As a nonlimiting example, a high pixel count image may contain 256 pixels, however a desired number of pixels may be 128. Processor 132 may downsample the high pixel count image to convert 256 pixels into 128 pixels. In one or more embodiments, processor 132 may be configured to perform downsampling on data. Downsampling, also known as decimation, may include removing every $N^{th}$ entry in a sequence of samples, all but every $N^{th}$ entry, or the like, which is a process known as "compression" and may be performed, for instance by an N-sample compressor implemented using hardware or software. Anti-aliasing and/or anti-imaging filters, and/or low-pass filters, may be used to eliminate side effects of compression.

With continued reference to FIG. 3, feature selection may include narrowing and/or filtering training data 304 to exclude features and/or elements, or training data including such elements that are not relevant to a purpose for which a trained machine learning model and/or algorithm is being trained, and/or collection of features, elements, or training data including such elements based on relevance to or utility for an intended task or purpose for which a machine learning model and/or algorithm is being trained. Feature selection may be implemented, without limitation, using any process described in this disclosure, including without limitation using training data classifiers, exclusion of outliers, or the like.

With continued reference to FIG. 3, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, wherein a difference between each value, X, and a minimum value, $X_{min}$, in a set or subset of values is divided by a range of values, $X_{max}-X_{min}$ in the set or subset:

$$X_{new} = \frac{X - X_{min}}{X_{max} - X_{min}}.$$

Feature scaling may include mean normalization, wherein a difference between each value, X, and a mean value of a set and/or subset of values, $X_{mean}$, is divided by a range of values, $X_{max}-X_{min}$, in the set or subset:

$$X_{new} = \frac{X - X_{mean}}{X_{max} - X_{min}}.$$

Feature scaling may include standardization, wherein a difference between X and $X_{mean}$ is divided by a standard deviation, $\sigma$, of a set or subset of values:

$$X_{new} = \frac{X - X_{mean}}{\sigma}.$$

Feature scaling may be performed using a median value of a set or subset, $X_{median}$, and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

A Person of ordinary skill in the art, upon reviewing the entirety of this disclosure, will be aware of various alternative or additional approaches that may be used for feature scaling.

With continued reference to FIG. 3, computing device, processor 132, and/or machine learning module 300 may be configured to perform one or more processes of data augmentation. For the purposes of this disclosure, "data augmentation" is a process that adds data to a training data 304 using elements and/or entries already in the dataset. Data augmentation may be accomplished, without limitation, using interpolation, generation of modified copies of existing entries and/or examples, and/or one or more generative artificial intelligence (AI) processes, for instance using deep neural networks and/or generative adversarial networks. Generative processes may be referred to alternatively in this context as "data synthesis" and as creating "synthetic data". Augmentation may include performing one or more transformations on data, such as geometric, color space, affine, brightness, cropping, and/or contrast transformations of images.

With continued reference to FIG. 3, machine learning module 300 may be configured to perform a lazy learning process and/or protocol 320. For the purposes of this disclosure, a "lazy learning" process and/or protocol is a process whereby machine learning is conducted upon receipt of input 312 to be converted to output 308 by combining the input 312 and training data 304 to derive the algorithm to be used to produce the output 308 on demand. A lazy learning process may alternatively be referred to as a "lazy loading" or "call-when-needed" process and/or protocol. For instance, an initial set of simulations may be performed to cover an initial heuristic and/or "first guess" at an output 308 and/or relationship. As a nonlimiting example, an initial heuristic may include a ranking of associations between inputs 312 and elements of training data 304. Heuristic may include selecting some number of highest-ranking associations and/or training data 304 elements. Lazy learning may implement any suitable lazy learning algorithm, including without limitation a k-nearest neighbors algorithm, a lazy naive Bayes algorithm, or the like. A person of ordinary skill in the art, upon reviewing the entirety of this disclosure, will be aware of various lazy learning algorithms that may be applied to generate outputs as described in this disclosure, including without limitation lazy learning applications of machine learning algorithms as described in further detail below.

With continued reference to FIG. 3, Alternatively and/or additionally, machine learning processes as described in this disclosure may be used to generate machine learning models 324. A "machine learning model", for the purposes of this disclosure, is a data structure representing and/or instantiating a mathematical and/or algorithmic representation of a relationship between inputs 312 and outputs 308, generated using any machine learning process including without limitation any process described above, and stored in memory. An input 312 is submitted to a machine learning model 324 once created, which generates an output 308 based on the relationship that was derived. For instance, and without limitation, a linear regression model, generated using a linear regression algorithm, may compute a linear combination of input data using coefficients derived during machine learning processes to calculate an output datum. As a further nonlimiting example, a machine learning model 324 may be generated by creating an artificial neural network, such as a convolutional neural network comprising an input layer of nodes, one or more intermediate layers, and an output layer of nodes. Connections between nodes may be created by "training" the network, in which elements from a training data 304 are applied to the input nodes, and a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning, as described in detail below.

With continued reference to FIG. 3, machine learning module 300 may perform at least a supervised machine learning process 328. For the purposes of this disclosure, a "supervised" machine learning process is a process with algorithms that receive training data 304 relating one or more inputs 312 to one or more outputs 308, and seek to generate one or more data structures representing and/or instantiating one or more mathematical relations relating input 312 to output 308, where each of the one or more mathematical relations is optimal according to some criterion specified to the algorithm using some scoring function. For instance, a supervised learning algorithm may include inputs 312 described above as inputs, and outputs 308 described above as outputs, and a scoring function representing a desired form of relationship to be detected between inputs 312 and outputs 308. Scoring function may, for instance, seek to maximize the probability that a given input 312 and/or combination thereof is associated with a given output 308 to minimize the probability that a given input 312 is not associated with a given output 308. Scoring function may be expressed as a risk function representing an "expected loss" of an algorithm relating inputs 312 to outputs 308, where loss is computed as an error function representing a degree to which a prediction generated by the relation is incorrect when compared to a given input-output pair provided in training data 304. Supervised machine learning processes may include classification algorithms as defined above. A person of ordinary skill in the art, upon reviewing the entirety of this disclosure, will be aware of various possible variations of at least a supervised machine learning process 328 that may be used to determine a relation between inputs and outputs.

With continued reference to FIG. 3, training a supervised machine learning process may include, without limitation, iteratively updating coefficients, biases, and weights based on an error function, expected loss, and/or risk function. For instance, an output 308 generated by a supervised machine learning process 328 using an input example in a training example may be compared to an output example from the training example; an error function may be generated based on the comparison, which may include any error function suitable for use with any machine learning algorithm described in this disclosure, including a square of a difference between one or more sets of compared values or the like. Such an error function may be used in turn to update one or more weights, biases, coefficients, or other parameters of a machine learning model through any suitable process including without limitation gradient descent processes, least-squares processes, and/or other processes described in this disclosure. This may be done iteratively and/or recursively to gradually tune such weights, biases, coefficients, or other parameters. Updates may be performed in neural networks using one or more back-propagation algorithms. Iterative and/or recursive updates to weights, biases, coefficients, or other parameters as described above may be performed until currently available training data 304 are exhausted and/or until a convergence test is passed. For the purposes of this disclosure, a "convergence test" is a test for a condition selected to indicate that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively and/or additionally, one or more errors and/or error function values evaluated in training iterations may be compared to a threshold.

With continued reference to FIG. 3, a computing device, processor 132, and/or machine learning module 300 may be configured to perform method, method step, sequence of method steps, and/or algorithm described in reference to this figure, in any order and with any degree of repetition. For instance, computing device, processor 132, and/or machine learning module 300 may be configured to perform a single step, sequence, and/or algorithm repeatedly until a desired or commanded outcome is achieved; repetition of a step or a sequence of steps may be performed iteratively and/or recursively using outputs 308 of previous repetitions as inputs 312 to subsequent repetitions, aggregating inputs 312 and/or outputs 308 of repetitions to produce an aggregate result, reduction or decrement of one or more variables such as global variables, and/or division of a larger processing task into a set of iteratively addressed smaller processing tasks. A computing device, processor 132, apparatus 100, or machine learning module 300 may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. A person of ordinary skill in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 3, machine learning process may include at least an unsupervised machine learning process 332. For the purposes of this disclosure, an unsupervised machine learning process is a process that derives inferences in datasets without regard to labels. As a result, an unsupervised machine learning process 332 may be free to discover any structure, relationship, and/or correlation provided in the data. Unsupervised processes 332 may not require a response variable, may be used to find interesting patterns and/or inferences between variables, to determine a degree of correlation between two or more variables, or the like.

With continued reference to FIG. 3, machine learning module 300 may be designed and configured to create machine learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include an elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to a person of ordinary skill in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought. Similar methods to those described above may be applied to minimize error functions, as will be apparent to a person of ordinary skill in the art upon reviewing the entirety of this disclosure.

With continued reference to FIG. 3, machine learning algorithms may include, without limitation, linear discriminant analysis. Machine learning algorithm may include quadratic discriminant analysis. Machine learning algorithms may include kernel ridge regression. Machine learning algorithms may include support vector machines, including without limitation support vector classification-based regression processes. Machine learning algorithms may include stochastic gradient descent algorithms, including classification and regression algorithms based on stochastic gradient descent. Machine learning algorithms may include nearest neighbors algorithms. Machine learning algorithms may include various forms of latent space regularization such as variational regularization. Machine learning algorithms may include Gaussian processes such as Gaussian Process Regression. Machine learning algorithms may include cross-decomposition algorithms, including partial least squares and/or canonical correlation analysis. Machine learning algorithms may include naive Bayes methods. Machine learning algorithms may include algorithms based on decision trees, such as decision tree classification or regression algorithms. Machine learning algorithms may include ensemble methods such as bagging meta-estimator, forest of randomized trees, AdaBoost, gradient tree boosting, and/or voting classifier methods. Machine learning algorithms may include neural net algorithms, including convolutional neural net processes.

With continued reference to FIG. 3, a machine learning model and/or process may be deployed or instantiated by incorporation into a program, apparatus, system, and/or module. For instance, and without limitation, a machine learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit, to represent a number according to any suitable encoding system including twos complement or the like, or may be stored in any volatile and/or non-volatile memory. Similarly, mathematical operations and input 312 and/or output 308 of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine learning process and/or model, including without limitation any combination of production and/or configuration of non-reconfigurable hardware elements, circuits, and/or modules such as without limitation application-specific integrated circuits (ASICs), production and/or configuration of reconfigurable hardware elements, circuits, and/or modules such as without limitation field programmable gate arrays (FPGAs), production and/or configuration of non-reconfigurable and/or non-rewritable memory elements, circuits, and/or modules such as without limitation non-rewritable read-only memory (ROM), other memory technology described in this disclosure, and/or production and/or configuration of any computing device and/or component thereof as described in this disclosure. Such deployed and/or instantiated machine learning model and/or algorithm may receive inputs 312 from any other process, module, and/or component described in this disclosure, and produce outputs 308 to any other process, module, and/or component described in this disclosure.

With continued reference to FIG. 3, any process of training, retraining, deployment, and/or instantiation of any machine learning model and/or algorithm may be performed and/or repeated after an initial deployment and/or instantiation to correct, refine, and/or improve the machine learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively and/or additionally, retraining, deployment, and/or instantiation may be event-based, and may be triggered, without limitation, by user inputs indicating sub-optimal or otherwise problematic performance and/or by automated field testing and/or auditing processes, which may compare outputs 308 of machine learning models and/or algorithms, and/or errors and/or error functions thereof, to any thresholds, convergence tests, or the like, and/or may compare outputs 308 of processes described herein to similar thresholds, convergence tests or the like. Event-based retraining, deployment, and/or instantiation may Alternatively and/or additionally be triggered by receipt and/or generation of one or more new training examples; a number of new training examples may be compared to a preconfigured threshold, where exceeding the preconfigured threshold may trigger retraining, deployment, and/or instantiation.

With continued reference to FIG. 3, retraining and/or additional training may be performed using any process for training described above, using any currently or previously deployed version of a machine learning model and/or algorithm as a starting point. Training data for retraining may be collected, preconditioned, sorted, classified, sanitized, or otherwise processed according to any process described in this disclosure. Training data 304 may include, without limitation, training examples including inputs 312 and correlated outputs 308 used, received, and/or generated from any version of any system, module, machine learning model or algorithm, apparatus, and/or method described in this disclosure. Such examples may be modified and/or labeled according to user feedback or other processes to indicate desired results, and/or may have actual or measured results from a process being modeled and/or predicted by system, module, machine learning model or algorithm, apparatus, and/or method as "desired" results to be compared to outputs 308 for training processes as described above. Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

With continued reference to FIG. 3, one or more processes or algorithms described above may be performed by at least a dedicated hardware unit 336. For the purposes of this disclosure, a "dedicated hardware unit" is a hardware component, circuit, or the like, aside from a principal control circuit and/or processor 132 performing method steps as described in this disclosure, that is specifically designated or selected to perform one or more specific tasks and/or processes described in reference to this figure, such as without limitation preprocessing and/or sanitization of training data and/or training a machine learning algorithm and/or model. Dedicated hardware unit 336 may include, without limitation, a hardware unit that can perform iterative or massed calculations, such as matrix-based calculations to update or tune parameters, weights, coefficients, and/or biases of machine learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously, in parallel, and/or the like. Such dedicated hardware units 336 may include, without limitation, graphical processing units (GPUs), dedicated signal processing modules, field programmable gate arrays (FPGA), other reconfigurable hardware that has been configured to instantiate parallel processing units for one or more specific tasks, or the like. Computing device, processor 132, apparatus 100, or machine learning module 300 may be configured to instruct one or more dedicated hardware units 336 to perform one or more operations described herein, such as evaluation of model and/or algorithm outputs, one-time or iterative updates to parameters, coefficients, weights, and/or biases, vector and/or matrix operations, and/or any other operations described in this disclosure.

Figure 4:
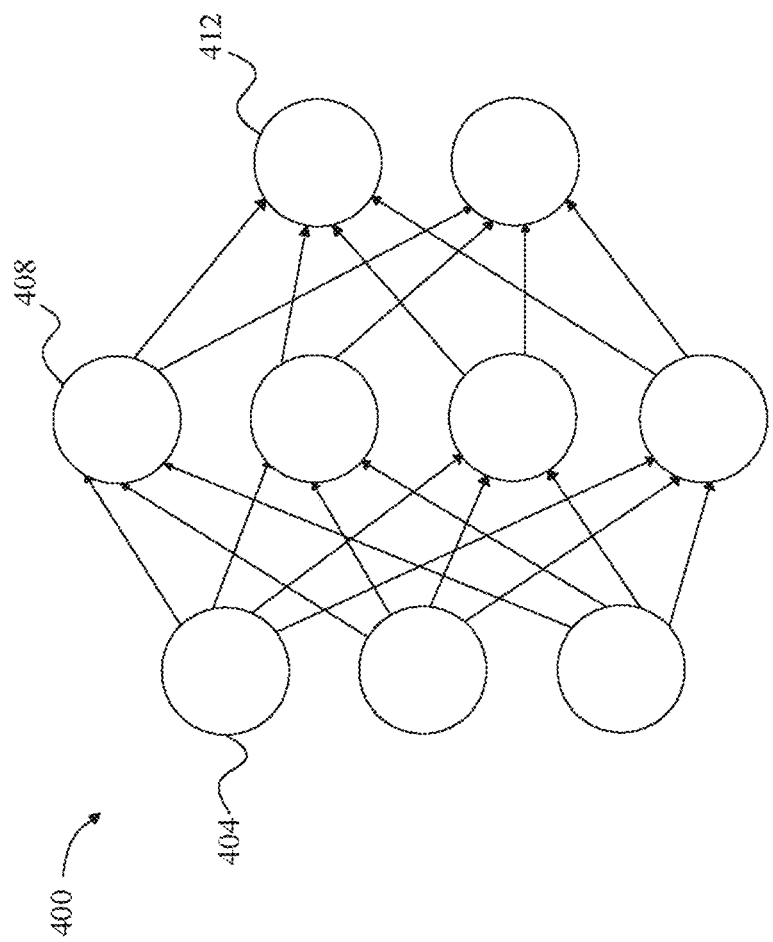
FIG. 4 is a block diagram of an exemplary embodiment of a neural network.

Referring now to FIG. 4, an exemplary embodiment of neural network 400 is illustrated. For the purposes of this disclosure, a neural network or artificial neural network is a network of "nodes" or data structures having one or more inputs, one or more outputs, and a function determining outputs based on inputs. Such nodes may be organized in a network, such as without limitation a convolutional neural network, including an input layer of nodes 404, at least an intermediate layer of nodes 408, and an output layer of nodes 412. Connections between nodes may be created via the process of "training" neural network 400, in which elements from a training dataset are applied to the input nodes, and a suitable training algorithm (such as Levenberg-Marquardt, conjugate gradient, simulated annealing, or other algorithms) is then used to adjust the connections and weights between nodes in adjacent layers of the neural network 400 to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network". As a further nonlimiting example, neural network 400 may include a convolutional neural network comprising an input layer of nodes 404, one or more intermediate layers of nodes 408, and an output layer of nodes 412. For the purposes of this disclosure, a "convolutional neural network" is a type of neural network 400 in which at least one hidden layer is a convolutional layer that convolves inputs to that layer with a subset of inputs known as a "kernel", along with one or more additional layers such as pooling layers, fully connected layers, and the like.

Figure 5:
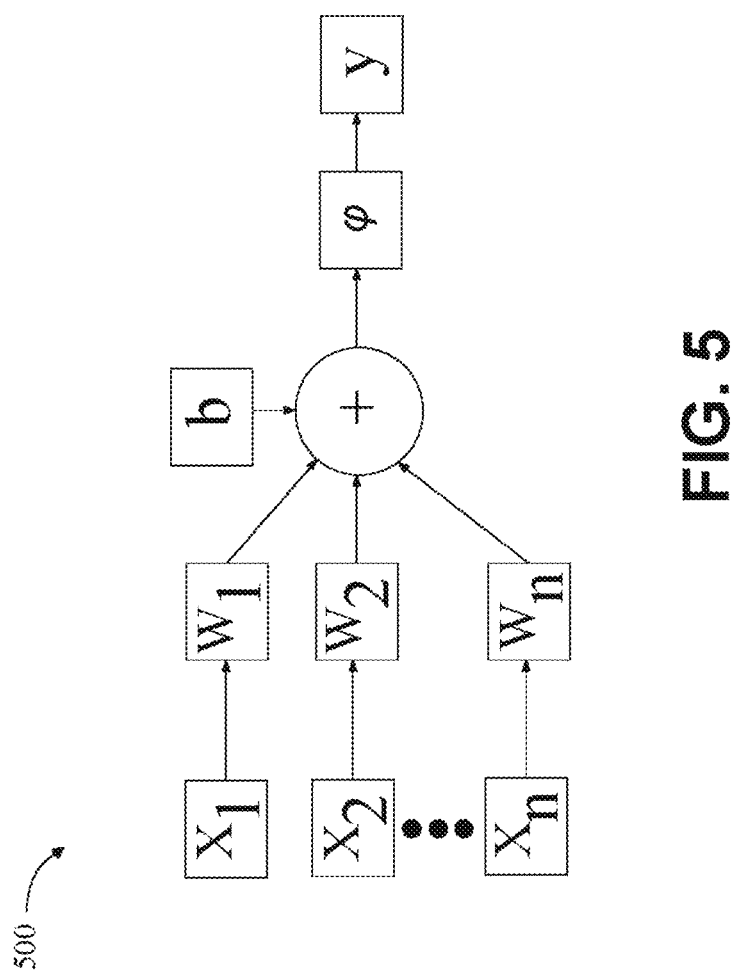
FIG. 5 is a block diagram of an exemplary embodiment of a node of a neural network.

Referring now to FIG. 5, an exemplary embodiment of a node 500 of neural network 400 is illustrated. Node 500 may include, without limitation, a plurality of inputs, $x_i$, that may receive numerical values from inputs to neural network 400 containing the node 500 and/or from other nodes 500. Node 500 may perform one or more activation functions to produce its output given one or more inputs, such as without limitation computing a binary step function comparing an input to a threshold value and outputting either a logic 1 or logic 0 output or its equivalent, a linear activation function whereby an output is directly proportional to input, and/or a nonlinear activation function wherein the output is not proportional to the input. Nonlinear activation functions may include, without limitation, a sigmoid function of the form $$f(x) = \frac{1}{1 - e^{-x}}$$

given input x, a tanh (hyperbolic tangent) function of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some value of a, an exponential linear units function such as $$f(x) = \begin{cases} x & \text{for } x \geq 0 \\ \alpha(e^x - 1) & \text{for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*sigmoid(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$, that may be used as activation functions. As a nonlimiting and illustrative example, node 500 may perform a weighted sum of inputs using weights, $w_i$, that are multiplied by respective inputs, $x_i$. Additionally and/or alternatively, a bias b may be added to the weighted sum of the inputs such that an offset is added to each unit in a neural network layer that is independent of the input to the layer. The weighted sum may then be input into a function, φ, which may generate one or more outputs, y. Weight, $w_i$, applied to an input, $x_i$, may indicate whether the input is "excitatory", indicating that it has strong influence on the one or more outputs, y, for instance by the corresponding weight having a large numerical value, or "inhibitory", indicating it has a weak influence on the one more outputs, y, for instance by the corresponding weight having a small numerical value. The values of weights, $w_i$, may be determined by training neural network 400 using training data, which may be performed using any suitable process as described above.

Figure 6:
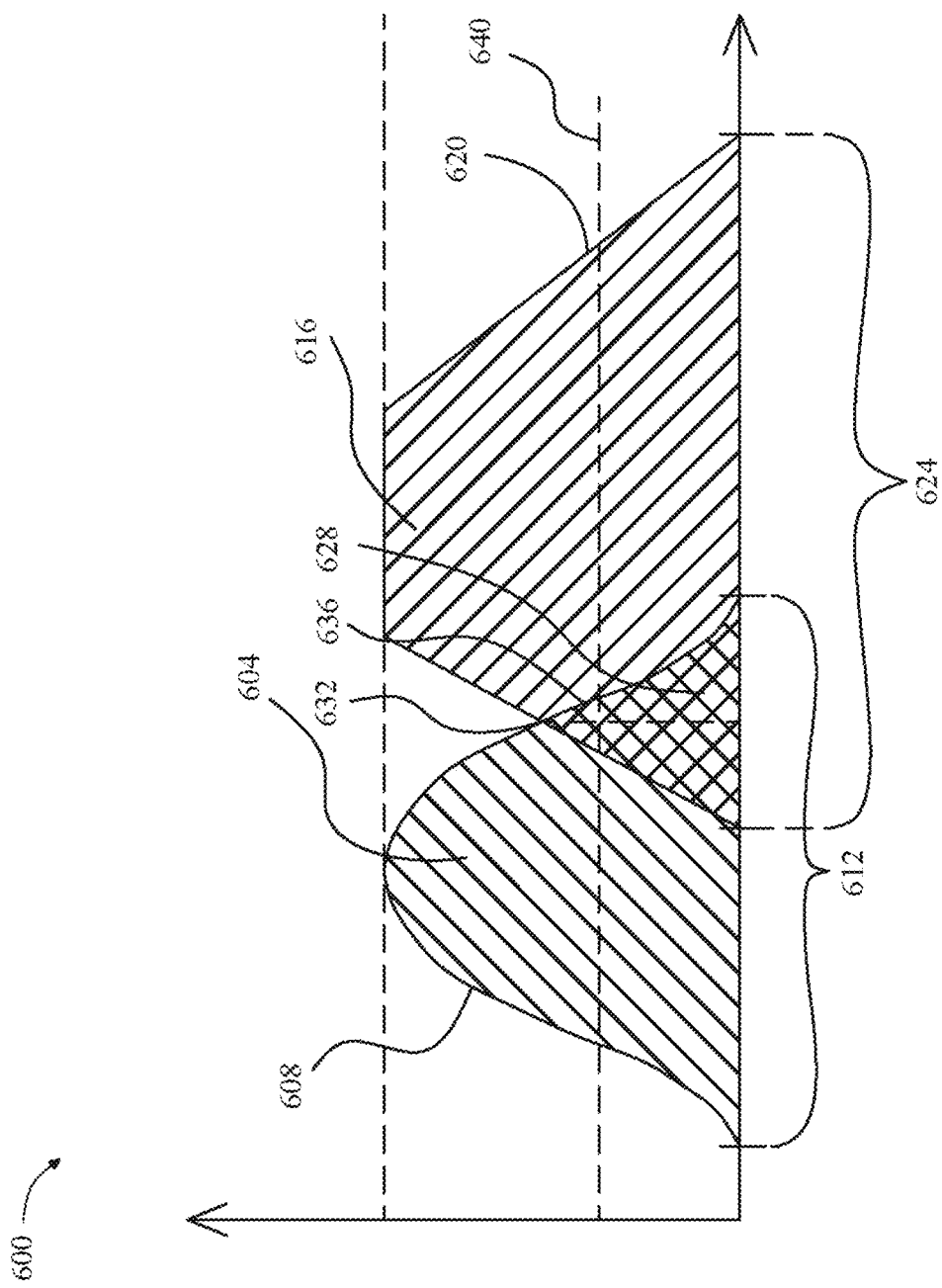
FIG. 6 is an illustration of an exemplary embodiment of fuzzy set comparison.

Referring now to FIG. 6, an exemplary embodiment of fuzzy set comparison 600 is illustrated. A first fuzzy set 604 may be represented, without limitation, according to a first membership function 608 representing a probability that an input falling on a first range of values 612 is a member of the first fuzzy set 604, where the first membership function 608 has values on a range of probabilities such as without limitation the interval [0,1], and an area beneath the first membership function 608 may represent a set of values within the first fuzzy set 604. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range of values 612 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \frac{x-a}{b-a}, \text{ for } a \leq x < b \\ \frac{c-x}{c-b}, \text{ if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

A person of ordinary skill in the art, upon reviewing the entirety of this disclosure, will be aware of various alternative or additional membership functions that may be used consistently with this disclosure.

With continued reference to FIG. 6, in one or more embodiments, first fuzzy set 604 may represent any value or combination of values as described above, including output from one or more machine learning models. A second fuzzy set 616, which may represent any value which may be represented by first fuzzy set 604, may be defined by a second membership function 620 on a second range 624; second range 624 may be identical and/or overlap with first range of values 612 and/or may be combined with first range via Cartesian product or the like to generate a mapping permitting evaluation overlap of first fuzzy set 604 and second fuzzy set 616. Where first fuzzy set 604 and second fuzzy set 616 have a region 628 that overlaps, first membership function 608 and second membership function 620 may intersect at a point 632 representing a probability, as defined on probability interval, of a match between first fuzzy set 604 and second fuzzy set 616. Alternatively, or additionally, a single value of first and/or second fuzzy set may be located at a locus 636 on first range of values 612 and/or second range 624, where a probability of membership may be taken by evaluation of first membership function 608 and/or second membership function 620 at that range point. A probability at 628 and/or 632 may be compared to a threshold 640 to determine whether a positive match is indicated. Threshold 640 may, in a nonlimiting example, represent a degree of match between first fuzzy set 604 and second fuzzy set 616, and/or single values therein with each other or with either set, which is sufficient for purposes of the matching process; for instance, threshold 640 may indicate a sufficient degree of overlap between an output from one or more machine learning models. Alternatively and/or additionally, each threshold 640 may be tuned by a machine learning and/or statistical process, for instance and without limitation as described in further detail in this disclosure.

With continued reference to FIG. 6, in one or more embodiments, a degree of match between fuzzy sets may be used to classify or label plurality of medical features 148, such as heart wall thickness 164, as described above in this disclosure. As a nonlimiting example, if one or more medical features 148 are associated with a fuzzy set that matches a fuzzy set of a cohort by having a degree of overlap exceeding a threshold, computing device may classify the one or more medical features as belonging to that cohort. Where multiple fuzzy matches are performed, degrees of match for each respective fuzzy set may be computed and aggregated through, for instance, addition, averaging, or the like, to determine an overall degree of match.

With continued reference to FIG. 6, in one or more embodiments, one or more one or more medical features 148 may be compared to multiple fuzzy sets of multiple cohorts. As a nonlimiting example, one or more medical features 148 may be represented by a fuzzy set that is compared to each of the multiple fuzzy sets of multiple cohorts, and a degree of overlap exceeding a threshold between the fuzzy set representing the one or more medical features 148 and any of the multiple fuzzy sets representing multiple cohorts may cause computing device to classify the one or more medical features 148 as belonging to that cohort. As a nonlimiting example, there may be two fuzzy sets representing two cohorts, cohort A and cohort B. Cohort A may have a cohort A fuzzy set, cohort B may have a cohort B fuzzy set, and one or more medical features 148 may have a medical feature fuzzy set. Computing device may compare medical feature fuzzy set with each of cohort A fuzzy set and cohort B fuzzy set, as described above, and classify one or more medical features 148 to either, both, or neither of cohort A fuzzy set and cohort B fuzzy set. Machine learning methods as described throughout this disclosure may, in a nonlimiting example, generate coefficients used in fuzzy set equations as described above, such as without limitation x, c, and σ of a Gaussian set as described above, as outputs of machine learning methods. Likewise, one or more medical features 148 may be used indirectly to determine a fuzzy set, as medical feature fuzzy set may be derived from outputs of one or more machine learning models that take one or more medical features 148 directly or indirectly as inputs.

With continued reference to FIG. 6, in one or more embodiments, fuzzy set comparison 600 may include a fuzzy inference model. For the purposes of this disclosure, a "fuzzy inference model" is a model that uses fuzzy logic to reach a decision and derive a meaningful outcome. As a nonlimiting example, a fuzzy inference system may be associated with various degrees of calcification at a heart valve, such as "Normal", "Mild", "Intermediate", and "Severe". In one or more embodiments, an inferencing rule may be applied to determine a fuzzy set membership of a combined output based on the fuzzy set membership of linguistic variables. As a nonlimiting example, membership of a combined output in a "Intermediate" fuzzy set may be determined based on a percentage membership of a second linguistic variable with a first mode in an "Intermediate" fuzzy set and a percentage membership of a second linguistic variable associated with a second mode in a "Mild" fuzzy set. In one or more embodiments, parameters of one or more medical features 148 may then be determined by comparison to a threshold or output using another defuzzification process. Each stage of such a process may be implemented using any type of machine learning model, such as any type of neural network, as described herein. In one or more embodiments, parameters of one or more fuzzy sets may be tuned using machine learning. In one or more embodiments, fuzzy inferencing and/or machine learning may be used to synthesize outputs of image processing machine learning model 172. In some cases, outputs such as medical features 148 may be combined to make an overall or final determination such as suggested modification, which may be displayed with or instead of individual outputs. As another nonlimiting example, outputs may be ranked, wherein the output with the highest confidence score or urgency may be the output displayed at display device 128 or displayed first in a ranked display of result outputs.

Figure 7:
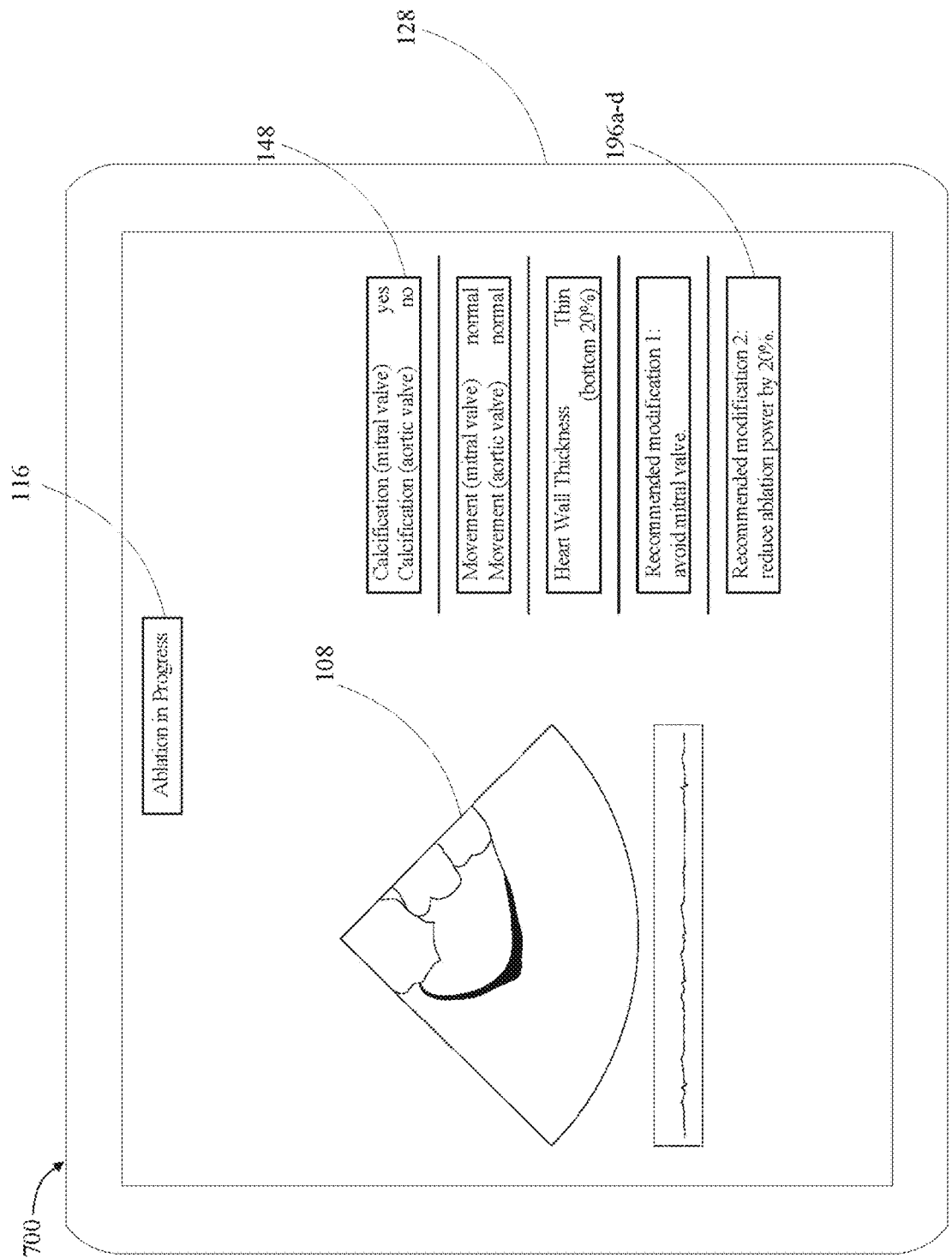
FIG. 7 is an illustration of an exemplary embodiments of a graphical user interface.

Referring now to FIG. 7, an exemplary embodiment of GUI 700 is illustrated. GUI 700 shows an exemplary session of apparatus 100 wherein concurrent medical procedure 116 includes ablation procedure 124. GUI 700 displays query image 108 that contains ICE. GUI 700 also summarizes the findings of apparatus 100 by displaying medical features 148 including a detected case of calcification 152 at the mitral valve, a detected case of a thin heart wall, as well as including possible abnormal valve functions 160 and calcification 152 at the aortic valve that are not currently detected. For the purposes of this disclosure, a "user interface" is a means by which a user and a computer system interact, for example, using input devices and software. User interface may include a graphical user interface (GUI), command line interface (CLI), menu-driven user interface, touch user interface, voice user interface (VUI), form-based user interface, any combination thereof, or the like. In one or more embodiments, a user may interact with user interface using computing device distinct from and communicatively connected to processor 132, such as a smartphone, tablet, or the like operated by the user. User interface may include one or more graphical locator and/or cursor facilities allowing user to interact with graphical models and/or combinations thereof, for instance using a touchscreen, touchpad, mouse, keyboard, and/or other manual data entry device. For the purposes of this disclosure, a "graphical user interface (GUI)" is a type of user interface that allows end users to interact with electronic devices through visual representations. In one or more embodiments, GUI may include icons, menus, other visual indicators or representations (graphics), audio indicators such as primary notation, display information, and related user controls. Menu may contain a list of choices and may allow users to select one from them. A menu bar may be displayed horizontally across the screen as a pull-down menu. Menu may include a context menu that appears only when user performs a specific action. Files, programs, web pages, and the like may be represented using a small picture within GUI. In one or more embodiments, GUI may include a graphical visualization of a user profile and/or the like. In one or more embodiments, processor 132 may be configured to modify and/or update GUI as a function of at least an input or the like by populating a user interface data structure and visually presenting data through modification of the GUI.

With continued reference to FIG. 7, in one or more embodiments, GUI may contain one or more interactive elements. For the purposes of this disclosure, an "interactive element" is an element within GUI that allows for communication with processor 132 by one or more users. For example, and without limitation, interactive elements may include a plurality of tabs wherein selection of a particular tab, such as for example, by using a fingertip, may indicate to a system to perform a particular function and display the result through GUI. In one or more embodiments, interactive element may include tabs within GUI, wherein the selection of a particular tab may result in a particular function. In one or more embodiments, interactive elements may include words, phrases, illustrations, and the like to indicate a particular process that one or more users would like system to perform. A person of ordinary skill in the art, upon reviewing the entirety of this disclosure, will be aware of various ways in which user interfaces, GUIs, and/or elements thereof may be implemented and/or used as described in this disclosure.

With continued reference to FIG. 7, in one or more embodiments, display device 128 and/or remote device may be configured to display at least an event handler graphic corresponding to at least an event handler. For the purposes of this disclosure, an "event handler graphic" is a graphical element with which user may interact using display device 128 and/or remote device to enter data, for instance and without limitation, one or more user inputs. Event handler graphic may include, without limitation, a button, a link, a checkbox, a text entry box and/or window, a drop-down list, a slider, or any other event handler graphic deemed suitable by a person of ordinary skill in the art upon reviewing the entirety of this disclosure. For the purposes of this disclosure, an "event handler" is a module, data structure, function, and/or routine that performs an action on display device 128 and/or remote device in response to one or more user inputs. For instance, and without limitation, event handler may record data corresponding to user selections of previously populated fields such as drop-down lists and/or text auto-complete and/or default entries, data corresponding to user selections of checkboxes, radio buttons, or the like, potentially along with automatically entered data triggered by such selections, user entry of textual data using a keyboard, touchscreen, speech-to-text program, or the like. Event handler may generate prompts for further information, may compare data to validation rules such as requirements that the data in question be entered within certain numerical ranges, and/or may modify data and/or generate warnings to user in response to such requirements. Event handler may convert data into expected and/or desired formats, for instance such as date formats, currency entry formats, name formats, or the like. Event handler may transmit data from a remote device to computing device.

With continued reference to FIG. 7, in one or more embodiments, event handler may include a cross-session state variable. For the purposes of this disclosure, a "cross-session state variable" is a variable recording data entered on remote device during a previous session. Such data may include, for instance, previously entered text, previous selections of one or more elements as described above, or the like. For instance, cross-session state variable data may represent a search that user entered in a past session. Cross-session state variable may be saved using any suitable combination of client-side data storage on remote device and server-side data storage on computing device; for instance, data may be saved wholly or in part as a "cookie" which may include data or an identification of remote device to prompt provision of cross-session state variable by the computing device, which may store the data on the computing device. Alternatively, or additionally, computing device may use login credentials, device identifier, and/or device fingerprint data to retrieve cross-session state variable, which the computing device may transmit to remote device. Cross-session state variable may include at least a prior session datum. A prior session datum may include any element of data that may be stored in cross-session state variable. Event handler graphic may be further configured to display at least a prior session datum, for instance and without limitation, by auto-populating user query data from previous sessions.

With continued reference to FIG. 7, in one or more embodiments, processor 132 and/or computing device may configure display device 128 and/or remote device to generate a graphical view. For the purposes of this disclosure, a "graphical view" is a data structure that results in display of one or more graphical elements on a screen. Graphical view may include at least a display element. For the purposes of this disclosure, a "display element" is an image that a program and/or data structure may cause to be displayed. Display elements may include, without limitation, windows, pop-up boxes, web browser pages, display layers, and/or any other display element deemed relevant by a person of ordinary skill in the art upon reviewing the entirety of this disclosure. Graphical view may include at least a selectable event graphic corresponding to one or more selectable event handlers. For the purposes of this disclosure, a "selectable event graphic" is a graphical element that, upon selection using a cursor or other locator as manipulated using a locator device such as a mouse, touchscreen, track pad, joystick, or the like, will trigger an action to be performed. As a nonlimiting example, a selectable event graphic may include a redirection link, defined as a hyperlink, button, image, portion of an image, and/or other graphic containing or referring to a uniform resource locator (URL) and/or other resource locator to another graphical view including without limitation buttons, and/or to a process that performs navigation to such URL and/or other resource locator upon selection of selectable event graphic. Redirection may be performed using any event handler, including without limitation event handlers detecting the click of a mouse or other locator, access of redirection link using a touchscreen, the selection of any key, mouseover events, or the like.

Figure 8:
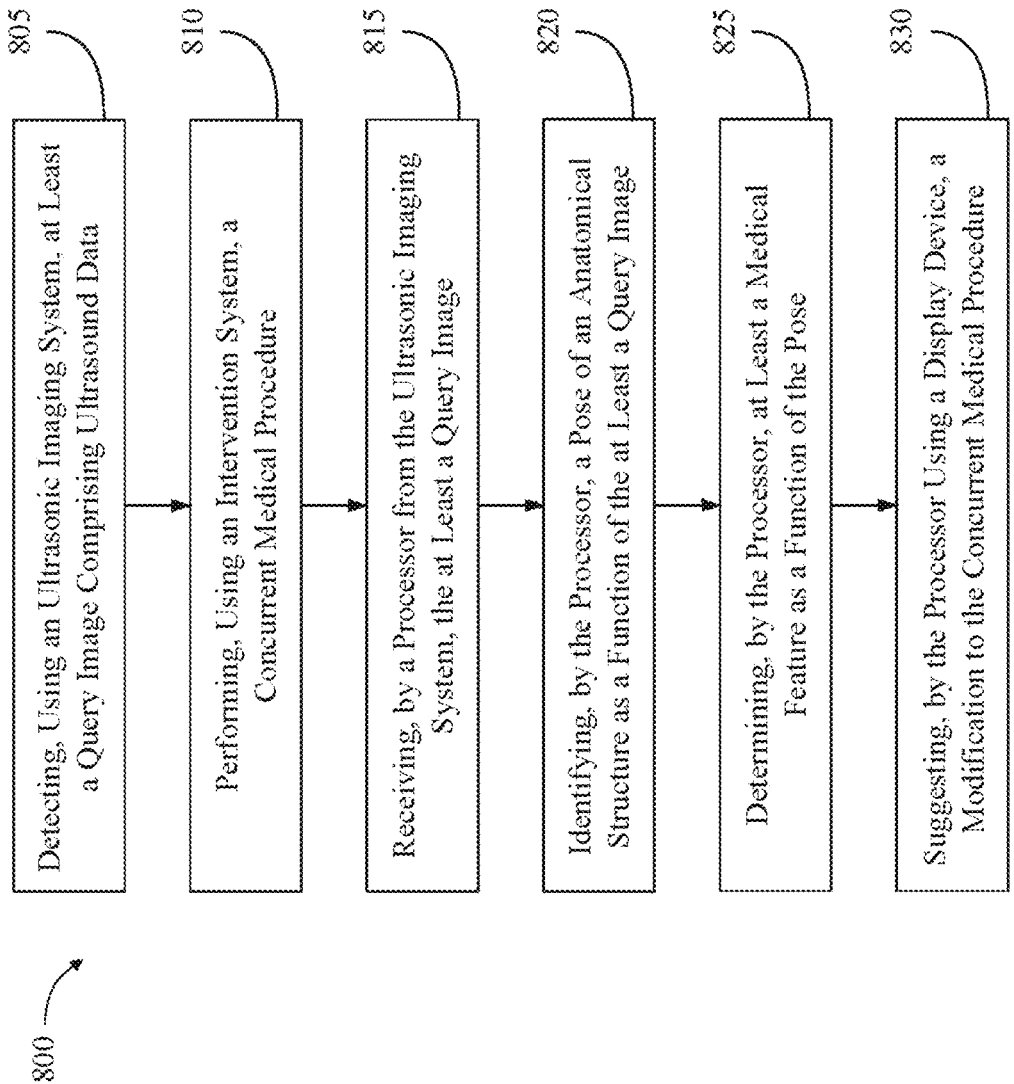
FIG. 8 is an exemplary flow diagram illustrating a method for identification of medical features.

Referring now to FIG. 8, an exemplary embodiment of a method 800 for identification of medical features is described. At step 805, method 800 includes detecting, using ultrasonic imaging system 104, at least a query image 108 comprising ultrasound data pertaining to a subject. This step may be implemented with reference to details described above in this disclosure and without limitation.

With continued reference to FIG. 8, at step 810, method 800 includes performing, using intervention system 112, concurrent medical procedure 116 as a function of the detection of the at least a query image 108. This step may be implemented with reference to details described above in this disclosure and without limitation.

With continued reference to FIG. 8, at step 815, method 800 includes receiving, by processor 132 from ultrasonic imaging system 104, at least a query image 108. This step may be implemented with reference to details described above in this disclosure and without limitation.

With continued reference to FIG. 8, at step 820, method 800 includes identifying, by processor 132, the pose 144 of anatomical structure as a function of at least a query image 108. This step may be implemented with reference to details described above in this disclosure and without limitation.

With continued reference to FIG. 8, at step 825, method 800 includes determining, by processor 132, at least a medical feature 148 as a function of the pose 144 of anatomical structure, wherein determining the at least a medical feature includes receiving feature training data 168 including plurality of training images as input and plurality of labelled features as output, training image processing machine learning model 172 including plurality of image processing algorithms 176 using the feature training data 168, and determining at least a medical feature 148 as a function of at least a query image 108 using the trained image processing machine learning model 172. This step may be implemented with reference to details described above in this disclosure and without limitation.

With continued reference to FIG. 8, at step 830, method 800 includes suggesting, by processor 132 using display device 128, modification 196*a-d* to concurrent medical procedure 116 as a function of at least a medical feature 148. This step may be implemented with reference to details described above in this disclosure and without limitation.

Figure 9:
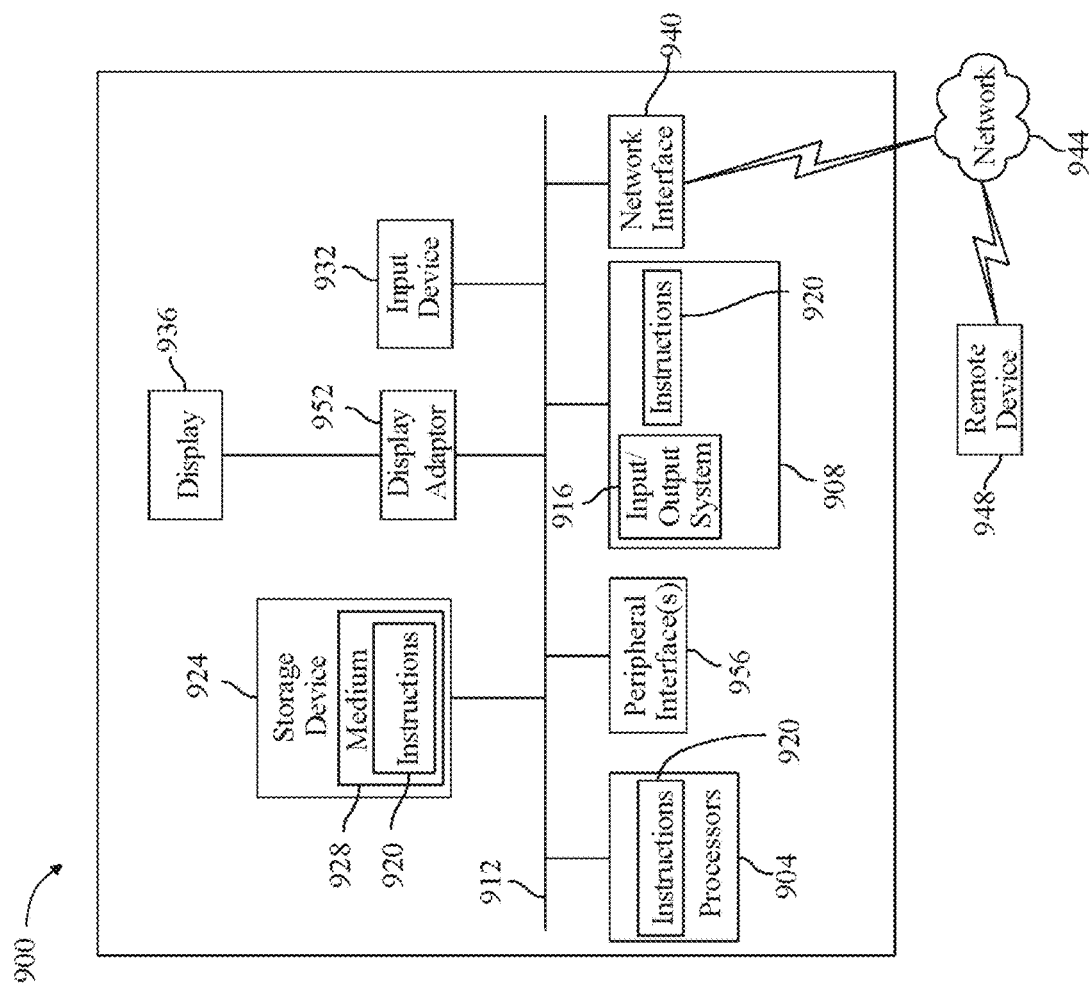
FIG. 9 is a block diagram of an exemplary embodiment of a computing system that can be used to implement any one or more of the methodologies disclosed herein and any one or more portions thereof.

Referring now to FIG. 9, it is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to one of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module. Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission. Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein. Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

With continued reference to FIG. 9, the figure shows a diagrammatic representation of one embodiment of a computing device in the exemplary form of a computing system 900 within which a set of instructions for causing the computing system 900 to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computing system 900 may include a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures. Processor 904 may include any suitable processor, such as without limitation a processor incorporating logical circuitry for performing arithmetic and logical operations, such as an arithmetic and logic unit, which may be regulated with a state machine and directed by operational inputs from memory and/or sensors; processor 904 may be organized according to Von Neumann and/or Harvard architecture as a nonlimiting example. Processor 904 may include, incorporate, and/or be incorporated in, without limitation, a microcontroller, microprocessor, digital signal processor, field programmable gate array, complex programmable logic device, graphical processing unit, general-purpose graphical processing unit, tensor processing unit, analog or mixed signal processor, trusted platform module, a floating-point unit, and/or system on a chip.

With continued reference to FIG. 9, memory 908 may include various components (e.g., machine-readable media) including, but not limited to, a random-access memory component, a read only component, and any combinations thereof. In one example, a basic input/output system 916, including basic routines that help to transfer information between elements within computing system 900, such as during start-up, may be stored in memory 908. Memory 908 (e.g., stored on one or more machine-readable media) may also include instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

With continued reference to FIG. 9, computing system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, small computer system interface, advanced technology attachment, serial advanced technology attachment, universal serial bus, IEEE 1394 (FIREWIRE), and any combinations thereof. In one example, storage device 924 (or one or more components thereof) may be removably interfaced with computing system 900 (e.g., via an external port connector (not shown)). Particularly, storage device 924 and an associated machine-readable medium 928 may provide nonvolatile and/or volatile storage of machine-readable instructions, data structures, program modules, and/or other data for computing system 900. In one example, software 920 may reside, completely or partially, within machine-readable medium 928. In another example, software 920 may reside, completely or partially, within processor 904.

With continued reference to FIG. 9, computing system 900 may also include an input device 932. In one example, a user of computing system 900 may enter commands and/or other information into computing system 900 via input device 932. Examples of input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display device 936, discussed further below. Input device 932 may be utilized as a user selection device for selecting one or more graphical representations in a graphical interface as described above.

With continued reference to FIG. 9, user may also input commands and/or other information to computing system 900 via storage device 924 (e.g., a removable disk drive, a flash drive, etc.) and/or network interface device 940. A network interface device, such as network interface device 940, may be utilized for connecting computing system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide-area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computing system 900 via network interface device 940.

With continued reference to FIG. 9, computing system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computing system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for identifying medical features, the apparatus comprising:
   an ultrasonic imaging system configured to detect at least a query image comprising ultrasound data pertaining to a subject;
   an intervention system configured to perform a concurrent medical procedure as a function of the detection of the at least a query image;
   a display device;
   a processor; and
   a memory communicatively connected to the processor, wherein the memory contains instructions configuring the processor to:
      receive, from the ultrasonic imaging system, the at least a query image;
      identify a pose of an anatomical structure as a function of the at least a query image, wherein identifying the pose of the anatomical structure comprises:
         locating at least a point of view (POV) as a function of the query image and a first subset of the plurality of image processing algorithms; and
         determining a view angle (VA) as a function of the at least a POV, wherein the at least a POV and the VA define at least a portion of the anatomical structure;
      determine at least a medical feature as a function of the pose of the anatomical structure, wherein determining the at least a medical feature comprises:
         receiving feature training data comprising a plurality of training images as input and a plurality of labelled features as output;
         training an image processing machine learning model comprising a plurality of image processing algorithms using the feature training data; and
         determining the at least a medical feature as a function of the at least a query image using the trained image processing machine learning model and a second subset of the plurality of image processing algorithms; and
      suggest, using the display device, a modification to the concurrent medical procedure as a function of the at least a medical feature.

2. The apparatus of claim 1, wherein:
   the intervention system comprises a catheter configured to perform an ablation procedure;
   determining the at least a medical feature comprises identifying a thrombus in a left atrial appendage of a heart; and
   suggesting the modification to the concurrent medical procedure comprises terminating the ablation procedure upon identifying the thrombus.

3. The apparatus of claim 2, wherein determining the at least a medical feature comprises identifying a case of calcification in a heart valve.

4. The apparatus of claim 3, wherein suggesting the modification to the concurrent medical procedure comprises avoiding, using the catheter, the heart valve upon identifying the case of calcification.

5. The apparatus of claim 1, wherein:
the plurality of labelled features comprises a plurality of heart valve functions; and
determining the at least a medical feature comprises:
classifying, using a classifier, the feature training data into a plurality of classes as a function of the plurality of heart valve functions, wherein each class of the plurality of classes shares at least one similar heart valve function; and
classifying an abnormal function of a heart valve as a function of the plurality of classes.

6. The apparatus of claim 1, wherein:
determining the at least a medical feature comprises determining a thickness pertaining to the anatomical structure;
the plurality of labelled features comprises a plurality of thicknesses; and
determining the at least a medical feature comprises:
labeling, using a labeling algorithm, the feature training data with a plurality of labels correlated with the plurality of thicknesses, wherein each label of the plurality of labels represents a thickness; and
determining the thickness as a function of the plurality of labels.

7. The apparatus of claim 6, wherein suggesting the modification to the concurrent medical procedure comprises adjusting at least a parameter of an ablation procedure as a function of the thickness.

8. The apparatus of claim 1, wherein the at least a query image comprises an intracardiac echocardiogram (ICE).

9. The apparatus of claim 1, wherein the at least a query image comprises a point-of-care ultrasound (POCUS).

10. A method for identifying medical features, the method comprising:
detecting, using an ultrasonic imaging system, at least a query image comprising ultrasound data pertaining to a subject;
performing, using an intervention system, a concurrent medical procedure as a function of the detection of the at least a query image;
receiving, by a processor from the ultrasonic imaging system, the at least a query image;
identifying, by the processor, a pose of an anatomical structure as a function of the at least a query image, wherein: identifying the pose of the anatomical structure comprises:
locating at least a POV as a function of the query image and a first subset of the plurality of image processing algorithms; and
determining a VA as a function of the at least a POV, wherein the at POV and the VA define at least a portion of the anatomical structure;
determining, by the processor, at least a medical feature as a function of the pose of an anatomical structure, wherein determining the at least a medical feature comprises:
receiving feature training data comprising a plurality of training images as input and a plurality of labelled features as output;
training an image processing machine learning model comprising a plurality of image processing algorithms using the feature training data; and
determining the at least a medical feature as a function of the at least a query image using the trained image processing machine learning model and a second subset of the plurality of image processing algorithms; and
suggesting, by the processor using a display device, a modification to the concurrent medical procedure as a function of the at least a medical feature.

11. The method of claim 10, wherein:
the intervention system comprises a catheter configured to perform an ablation procedure;
determining the at least a medical feature comprises identifying a thrombus in a left atrial appendage of a heart; and
suggesting the modification to the concurrent medical procedure comprises terminating the ablation procedure upon identifying the thrombus.

12. The method of claim 11, wherein determining the at least a medical feature comprises identifying a case of calcification in a heart valve.

13. The method of claim 12, wherein suggesting the modification to the concurrent medical procedure comprises avoiding, using the catheter, the heart valve upon identifying the case of calcification.

14. The method of claim 10, wherein:
the plurality of labelled features comprises a plurality of heart valve functions; and
determining the at least a medical feature comprises:
classifying, using a classifier, the feature training data into a plurality of classes as a function of the plurality of heart valve functions, wherein each class of the plurality of classes shares at least one similar heart valve function; and
classifying an abnormal function of a heart valve as a function of the plurality of classes.

15. The method of claim 10, wherein:
determining the at least a medical feature comprises determining a thickness pertaining to the anatomical structure;
the plurality of labelled features comprises a plurality of thicknesses; and
determining the at least a medical feature comprises:
labeling, using a labeling algorithm, the feature training data with a plurality of labels correlated with the plurality of thicknesses, wherein each label of the plurality of labels represents a thickness; and
determining the thickness as a function of the plurality of labels.

16. The method of claim 15, wherein suggesting the modification to the concurrent medical procedure comprises adjusting at least a parameter of an ablation procedure as a function of the thickness.

17. The method of claim 10, wherein the at least a query image comprises an intracardiac echocardiogram (ICE).

18. The method of claim 10, wherein the at least a query image comprises a point-of-care ultrasound (POCUS).

19. An apparatus for identifying medical features, the apparatus comprising:
an ultrasonic imaging system configured to detect at least a query image comprising ultrasound data pertaining to a subject;
an intervention system configured to perform a concurrent medical procedure as a function of the detection of the at least a query image;
a display device;
a processor; and a memory communicatively connected to the processor, wherein the memory contains instructions configuring the processor to:
  receive, from the ultrasonic imaging system, the at least a query image;
  identify a pose of an anatomical structure as a function of the at least a query image;
  determine at least a medical feature as a function of the pose of the anatomical structure, wherein determining the at least a medical feature comprises:
    receiving feature training data comprising a plurality of training images as input and a plurality of labelled features as output, wherein the plurality of labelled features comprises a plurality of heart valve functions;
    classifying, using a classifier, the feature training data into a plurality of classes as a function of the plurality of heart valve functions, wherein each class of the plurality of classes shares at least one similar heart valve function;
    classifying an abnormal function of a heart valve as a function of the plurality of classes;
    training an image processing machine learning model comprising a plurality of image processing algorithms using the feature training data; and
    determining the at least a medical feature as a function of the at least a query image using the trained image processing machine learning model; and
  suggest, using the display device, a modification to the concurrent medical procedure as a function of the at least a medical feature.

20. A method for identifying medical features, the method comprising:

detecting, using an ultrasonic imaging system, at least a query image comprising ultrasound data pertaining to a subject;
performing, using an intervention system, a concurrent medical procedure as a function of the detection of the at least a query image;
receiving, by a processor from the ultrasonic imaging system, the at least a query image;
identifying, by the processor, a pose of an anatomical structure as a function of the at least a query image;
determining, by the processor, at least a medical feature as a function of the pose of an anatomical structure, wherein determining the at least a medical feature comprises:
  receiving feature training data comprising a plurality of training images as input and a plurality of labelled features as output wherein the plurality of labelled features comprises a plurality of heart valve functions;
  classifying, using a classifier, the feature training data into a plurality of classes as a function of the plurality of heart valve functions, wherein each class of the plurality of classes shares at least one similar heart valve function;
  classifying an abnormal function of a heart valve as a function of the plurality of classes;
  training an image processing machine learning model comprising a plurality of image processing algorithms using the feature training data; and
  determining the at least a medical feature as a function of the at least a query image using the trained image processing machine learning model; and
suggesting, by the processor using a display device, a modification to the concurrent medical procedure as a function of the at least a medical feature.

* * * * *